(12) United States Patent
O'Hara

(10) Patent No.: US 11,197,938 B1
(45) Date of Patent: Dec. 14, 2021

(54) SYSTEM AND PROCESS FOR PRODUCTION OF ISOTOPES AND ISOTOPE COMPOSITIONS

(71) Applicant: Battelle Memorial Institute, Richland, WA (US)

(72) Inventor: Matthew J. O'Hara, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 752 days.

(21) Appl. No.: 15/788,724

(22) Filed: Oct. 19, 2017

Related U.S. Application Data

(60) Provisional application No. 62/410,303, filed on Oct. 19, 2016.

(51) Int. Cl.
| | |
|---|---|
| *A61K 51/00* | (2006.01) |
| *A61K 51/10* | (2006.01) |
| *B01D 59/30* | (2006.01) |
| *G21G 1/00* | (2006.01) |
| *C01G 25/00* | (2006.01) |
| *G21G 4/08* | (2006.01) |
| *C22B 3/20* | (2006.01) |

(52) U.S. Cl.
CPC .............. *A61K 51/10* (2013.01); *B01D 59/30* (2013.01); *C01G 25/003* (2013.01); *C22B 3/20* (2013.01); *G21G 1/001* (2013.01); *G21G 4/08* (2013.01)

(58) Field of Classification Search
CPC .... B01D 59/30; C01G 25/003; C22B 3/0004; G21G 2001/0094; G21G 4/08; A61K 51/10
USPC .......................................................... 423/2
See application file for complete search history.

(56) References Cited

U.S. PATENT DOCUMENTS

| 5,512,256 A | 4/1996 | Bray et al. | |
|---|---|---|---|
| 6,972,414 B2 | 12/2005 | Egorov et al. | |
| 7,554,098 B2 | 6/2009 | O'Hara et al. | |
| 2017/0015685 A1* | 1/2017 | Sato | ........................ G01N 33/60 |

OTHER PUBLICATIONS

Zweit et al, "Production of No-carrier-added zirconium-89 for positron emission tomography" Appl. Radiat. Isot. vol. 42, No. 2, pp. 199-201, 1991. (Year: 1991).*
Adam et al., "Consensus Nomenclature Rules for Radiopharmaceutical Chemistry—Setting the Record Straight", Society of Radiopharmaceutical Sciences, Apr. 2017, Fredericksburg, TX, 15 pages.
Aguilar-Arteaga et al., "Magnetic Solids in Analytical Chemistry: A Review", Analytica Chimica Acta vol. 674, 2010, Netherlands, pp. 157-165.
Aneheim et al., "Automated Astatination of Biomolecules—A Stepping Stone Towards Multicenter Clinical Trials", Scientific Reports 5:12025, 2015, United Kingdom, 11 pages.
Bhattacharyya et al., "Zirconium 89 Labeled Panitumumab: A Potential Immuno-PET Probe for HER1-Expressing Carcinomas", Nuclear Medicine and Biology vol. 40, 2013, Netherlands, pp. 451-457.
Bio-Rad, "AG1, AG MP-1 and AG 2 Strong Anion Exchange Resin Instruction Manual", Bio-Rad Laboratories, LIT212 Rev C, Hercules, CA, 23 pages. (no date available).
Börjesson et al., "Performance of Immuno-Positron Emission Tomography with Zirconium-89-Labeled Chimeric Monoclonal Antibody U36 in the Detection of Lymph Node Metastases in Head and Neck Cancer Patients", Clinical Cancer Research vol. 12, 2006, United States, pp. 2133-2140.
Boros et al., "Chelate-Free Metal Ion Binding and Heat-Induced Radiolabeling of Iron Oxide Nanoparticles", The Royal Society of Chemistry, Chemical Science vol. 6, 2015, United Kingdom, pp. 225-236.
Brand-Williams et al., "Use of a Free Radical Method to Evaluate Antioxidant Activity", LWT-Food Science and Technology vol. 28, 1995, United States, pp. 25-30.
Chen et al., "In Vivo Integrity and Biological Fate of Chelator-Free Zirconium-89-Labeled Mesoporous Silica Nanoparticles", ACS Nano vol. 9, No. 8, 2015, United States, pp. 7950-7959.
Ciarmatori et al., "Some Experimental Studies on 89Zr Production", Radiochimica Acta vol. 99, 2011, Germany, pp. 631-634.
Dejesus et al., "Production and Purification of 89Zr, a Potential PET Antibody Label", Applied Radiation and Isotopes vol. 41, No. 8, 1990, United Kingdom, pp. 789-790.
Dutta et al., "Production of 88,89Zr by Proton induced Activation of natY and Separation by SLX and LLX", Journal of Radioanalytical and Nuclear Chemistry vol. 281, 2009, Hungary, pp. 663-667.
Fischer et al., "89Zr, a Radiometal Nuclide with High Potential for Molecular Imaging with PET: Chemistry, Applications and Remaining Challenges", Molecules vol. 18, 2013, Switzerland, pp. 6469-6490.
Gaykema et al., "89Zr-trastuzumab and 89Zr-bevacizumab PET to Evaluate the Effect of the HSP90 Inhibitor NVP-AUY922 in Metastatic Breast Cancer Patients", Clinical Cancer Research vol. 20, Aug. 2014, United States, pp. 3945-3954.
Gómez-Vallejo et al., "Specific Activity of 11C-Labelled Radiotracers: A Big Challenge for PET Chemists", Chapter 7, Positron Emission Tomography—Current Clinical and Research Aspects, Hsieh (Ed.), Intech, Feb. 2012, Croatia, pp. 183-210.
Holland et al., "Standardized Methods for the Production of High Specific-Activity Zirconmium-89", Nuclear Medicine and Biology vol. 36, 2009, Netherlands, pp. 729-739.
Holland et al., "Unconventional Nuclides for Radiopharmaceuticals", Molecular Imaging vol. 9, No. 1, 2010, United States, pp. 1-20.
Hua et al., "Heavy Metal Removal from Water/Wastewater by Nanosized Metal Oxides: A Review", Journal of Hazardous Materials vol. 211-212, 2012, Netherlands, pp. 317-331.
Hudson et al., "Bare Magnetic Nanoparticles: Sustainable Synthesis and Applications in Catalytic Organic Transformations", Green Chemistry vol. 16, No. 10, Oct. 2014, United Kingdom, pp. 4493-4505.

(Continued)

*Primary Examiner* — Steven J Bos
(74) *Attorney, Agent, or Firm* — Wells St. John P.S.

(57) ABSTRACT

Methods for purifying $^{89}$Zr are provided, $^{89}$Zr compositions are provided, isotope compositions are provided that can include: a radio isotope and a nanoparticle, and methods for radio labeling monoclonal antibodies are provided.

4 Claims, 23 Drawing Sheets

(56) References Cited

OTHER PUBLICATIONS

Indira et al., "Magnetic Nanoparticles—A Review", International Journal of Pharmaceutical Sciences and Nanotechnology vol. 3, Issue 3, Oct.-Dec. 2010, India, pp. 1035-1042.
Jacobson et al., "Fluorine-18 Radiochemistry, Labeling Strategies and Synthetic Routes", Bioconjugate Chemistry 26, 2015, United States, pp. 1-18.
Jauw et al., "Immuno-Positron Emission Tomography with Zirconium-89-Labeled Monoclonal Antibodies in Oncology: What Can We Learn from Initial Clinical Trials?", Frontiers in Pharmacology vol. 7, May 2016, Switzerland, 15 pages.
Karmani et al., "Antibody-Functionalized Nanoparticles for Imaging Cancer: Influence of Conjugation to Gold Nanoparticles on the Biodistribution of 89Zr-Labeled Cetuximab in Mice", Contrast Media and Molecular Imaging vol. 8, 2013, United States, pp. 402-408.
Kasbollah et al., "Review on Production of 89Zr in a Medical Cyclotron for PET Radiopharmaceuticals", Journal of Nuclear Medicine Technology vol. 41, Mar. 2013, United States, pp. 35-41.
Kaur et al., "Conjugates of Magnetic Nanoparticle-Actinide Specific Chelator for Radioactive Waste Separation", Environmental Science & Technology vol. 47, 2013, United States, pp. 11942-11959.
Lee, "Immuno-PET for Tumor Targeting", The Journal of Nuclear Medicine vol. 44, No. 8, Aug. 2003, China, pp. 1282-1283.
Lin et al., "Semi-Automated Production of 89Zr-oxalate/89Zr-chloride and the Potential of 89Zr-chloride in Radiopharmaceutical Compounding", Applied Radiation and Isotopes vol. 107, 2016, United Kingdom, pp. 317-322.
Link et al., "A Practical High Current 11 MeV Production of High Specific Activity 89Zr", Proceedings of the 15th International Workshop on Targetry and Target Chemistry, Aug. 20, 2014, Prague, Czech Republic, 1 page.
Mastren et al., "Specific Activity Measurement of 64Cu: A Comparison of Methods", Applied Radiation and Isotopes vol. 90, Aug. 2014, United Kingdom, pp. 117-121.
Meijs et al., "Production of Highly Pure No-Carrier Added 89Zr for the Labelling of Antibodies with a Position Emitter", Applied Radiation and Isotopes vol. 45, 1994, United Kingdom, pp. 1143-1147.
Menini et al., "Cobalt- and Manganese-Substituted Ferrites as Efficient Single-Site Heterogeneous Catalysts for Aerobic Oxidation of Monoterpenic Alkenes under Solvent-Free Conditions", Journal of Catalysis vol. 254, 2008, United States, pp. 355-364.
Menke-van der Houven van Oordt et al., "89Zr-cetuximab PET Imaging in Patients with Advanced Colorectal Cancer", Oncotarget vol. 6, 2015, United States, pp. 30384-30393.
Miller et al., "Synthesis, Characterization, and Biodistribution of Multiple 89Zr-Labeled Pore-Expanded Mesoporous Silica Nanoparticles for PET", Nanoscale, 2014, United Kingdom, 16 pages.
Milonjic et al., "The Point of Zero Charge and Adsorption Properties of Natural Magnetite", Journal of Radioanalytical Chemistry vol. 78, Mar. 1983, Hungary, pp. 15-24.
Muylle et al., "Tumour Targeting and Radiation Dose of Radioimmunotherapy with 90Y-rituximab in CD20+ B-cell Lymphoma as Predicted by 89Zr-rituximab Immuno-PET: Impact of Preloading with Unlabelled Rituximab", Eur J Nucl Med Mol Imaging vol. 42, 2015, Germany, pp. 1304-1314.
Nassar, "Iron Oxide Nanoadsorbents for Removal of Various Pollutants from Wastewater: An Overview", Chapter 3 of Application of Adsorbents for Water Pollution Control, Amit Bhatnagar (Ed.), Bentham Science Publishers, 2012, United States, pp. 81-118.
National Nuclear Data Center, "Information Extracted from the NuDat 2 Database", Brookhaven National Laboratory, Upton, NY, available online at www.nndc.bnl.gov, Dec. 2015, 1 page.
National Nuclear Data Center, "Information Extracted from the NuDat 2 Database", Brookhaven National Laboratory, Upton, NY, available online at www.nndc.bnl.gov, Mar. 2016, 1 page.
National Nuclear Data Center, "Information Extracted from the NuDat 2 Database", Brookhaven National Laboratory, Upton, NY, available online at www.nndc.bnl.gov, Sep. 2015, 1 page.
National Nuclear Data Center, "Information Extracted from the NuDat 2 Database", Brookhaven National Laboratory, Upton, NY, available online at www.nndc.bnl.gov, Sep. 2017, 1 page.
O'Hara et al., "Magnetic Iron Oxide and Manganese-Doped Iron Oxide Nanoparticles for the Collection of Alpha-Emitting Radionuclides from Aqueous Solutions", RSC Advances, 2016, United Kingdom, 40 pages.
Petrova et al., "The Magnetite as Adsorbent for some Hazardous Species from Aqueous Solutions: A Review", International Review of Chemical Engineering vol. 3, No. 2, Mar. 2011, Italy, pp. 134-152.
Poniger et al., "Automated Production of 124I and 64Cu using IBA Terimo and Pinctada Metal Electroplating and Processing Modules", Proceedings of the 14th International Workshop on Targetry and Target Chemistry, 2012, Mexico, pp. 114-119.
Poniger et al., "Fully Automated Production of Zr-89 using IBA Nirta and Pinctada Systems", Proceedings of the 15th International Workshop on Targetry and Target Chemistry, 2014, Czech Republic, 4 pages.
Poriel et al., "Zirconium and Hafnium Separation, Part 1. Liquid/Liquid Extraction in Hydrochloric Acid Aqueous Solution with Aliquat 336", Separation Science and Technology vol. 41, 2006, United States, pp. 1927-1940.
Poriel et al., "Zirconium and Hafnium Separation, Part 2. Solid/Liquid Extraction in Hydrochloric Acid Aqueous Solution with Anion Exchange Resins", Separation Science and Technology vol. 41, 2006, United States, pp. 2711-2722.
Rice et al., "The Next Generation of Positron Emission Tomography Radiopharmaceuticals in Oncology", Seminars in Nuclear Medicine vol. 41, 2011, United Kingdom, pp. 265-282.
RxList: The Internet Drug Index, "Feraheme", available online at http://www.rxlist.com/feraheme-drug.htm, accessed Jul. 15, 2016, 3 pages.
Sadeghi et al., "Accelerator Production of the Positron Emitter Zirconium-89", Annals of Nuclear Energy vol. 41, 2012, United Kingdom, pp. 97-103.
Scharli et al., "Establishing Reliable Production of the PET Isotope 89Zr for Research Use: From Target Fabrication to Preclinical Imaging", Proceedings of the 14th International Workshop on Targetry and Target Chemistry, 2012, Mexico, 2012, pp. 101-107.
Sham et al., "Glypican-3-Targeting F(ab')2 for 89Zr PET of Hepatocellular Carcinoma", The Journal of Nuclear Medicine vol. 55, No. 12, Dec. 2014 China, 6 pages.
Siikanen et al., "A Peristaltic Pump Driven 89Zr Separation Module", Proceedings of the 14th International Workshop on Targetry and Target Chemistry, 2012, Mexico, 2012, pp. 206-210.
Svensson, "Production of 89Zr for Labelling of Antibodies to be Evaluated Preclinically with Micro-PET for Radioimmunodiagnostics of Prostate Cancer", Master of Science Thesis, Lund University, 2008, Sweden, 62 pages.
Taghilo et al., "Cyclotron Production of 89Zr: A Potent Radionuclide for Positron Emission Tomography", International Jounal of Physical Sciences vol. 7, Feb. 2012, Nigeria, pp. 1321-1325.
Trubert et al., "Behaviour of Zr, Hf, Hb, Ta and Pa on Macroporous Anion Exchanger in Chloride-Fluoride Media", Analytica Chimica Acta vol. 374, 1998, Netherlands, pp. 149-158.
Van de Watering et al., "Zirconium-89 Labeled Antibodies: A New Tool for Molecular Imaging in Cancer Patients", BioMed Research International vol. 2014, 2014, United States, 13 pages.
Van Dongen et al., "Immuno-PET: A Navigator in Monoclonal Antibody Development and Applications", The Oncologist vol. 12, 2007, United States, pp. 1379-1389.
Verel et al., "89Zr Immuno-PET: Comprehensive Procedures for the Production of 89Zr-Labeled Monoclonal Antibodies", The Journal of Nuclear Medicine vol. 44, Aug. 2003, China, pp. 1271-1281.
Verel et al., "The Promise of Immuno-PET in Radioimmunotherapy", The Journal of Nuclear Medicine vol. 46, Jan. 2005, United States, pp. 164S-171S.
Viola-Villegas et al., "Noninvasive Imaging of PSMA in Prostate Tumors with 89Zr-Labeled huJ591 Engineered Antibody Frag-

(56) References Cited

OTHER PUBLICATIONS ments: The Faster Alternatives", Molecular Pharmaceutics vol. 11, 2014, United States, pp. 3965-3973.
Wooten et al., "Routine Production of 89Zr Using an Automated Module", Applied Sciences vol. 3, Jul. 2013, Switzerland, pp. 593-613.
Yang et al., "cRGD-Functionalized, DOX-Conjugated, and 64Cu-Labeled Superparamagnetic Iron Oxide Nanoparticles for Targeted Anticancer Drug Delivery and PET/MR Imaging", Biomaterials vol. 32, 2011, United Kingdom, pp. 4151-4160.
Zeglis et al., "The Bioconjugation and Radiosynthesis of 89Zr-DFO-Labeled Antibodies", Journal of Visualized Experiments 96, Feb. 2015, United States, 8 pages.
Baroncelli et al., "The Complexing Power of Hydroxamic Acids and its Effect on the Behaviour of Organic Extractants in the Reprocessing of Irradiated Fuels", Journal of Inorganic and Nuclear Chemistry vol. 27, May 1965, Ireland, pp. 1085-1092.
Bartos et al., "Synthesis and Ion-Exchange Properties of Manganese(IV) Dioxide Doped by 3+ Transition Metal Cations", Solvent Extraction and Ion Exchange vol. 19, Feb. 2007, Untied States, pp. 553-564.
Bray et al., "Development of a Unique Bismuth (Bi-213) Automated Generator for Use in Cancer Therapy", Industrial & Engineering Chemistry Research vol. 39, 2000, United States, pp. 3189-3194.
Burnett et al., "Pre-Concentration of Short-Lived Radionuclides using Manganese Dioxide Precipitation from Surface Waters", Journal of Radioanalytical and Nuclear Chemistry vol. 292, Issue 1, Apr. 2012, Hungary, pp. 25-28.
Chakravarty et al., "Removal of Arsenic from Groundwater using Low Cost Ferruginous Manganese Ore", Water Research vol. 36, Issue 3, Feb. 2002, Netherlands, pp. 625-632.
Cheal et al., "Pairwise Comparison of 89Zr- and 124I-Labeled cG250 Based on Positron Emission Tomography Imaging and Nonlinear Immunokinetic Modeling: . . . ", Eur J Nucl Med Mol Imaging, vol. 41, 2014, Germany, pp. 985-994.
Das et al., "Sorption of Uranium on Magnetite Nanoparticles", Journal of Radioanalytical and Nuclear Chemistry vol. 285, Sep. 2010, Hungary, pp. 447-454.
Deri et al., "PET Imaging with 89Zr: From Radiochemistry to the Clinic", Nuclear Medicine and Biology vol. 40, Jan. 2013, Netherlands, pp. 3-14.
Füchtner et al., "Factors Affecting the Specific Activity of [18F]Fluoride from a [18O]Water Target", Nuklearmedizin 47, 2008, Germany, pp. 116-119.
Grate et al., "Automated Radiochemical Separation, Analysis, and Sensing", Chapter 18, Handbook of Radioactivity Analysis, 3rd Edition, L'Annunziata (Ed.), Academic Press, 2012, United States, pp. 1179-1207.
Hernlem et al., "Stability Constants for Complexes of the Siderophore Desferrioxamine B with Selected Heavy Metal Cations", Inorganica Chimica Acta vol. 244, Mar. 1996, Netherlands, pp. 179-184.
Herscheid et al., "Manganese-52m for Direct Application: A New 52Fe/52mMn Generator Based on a Hydroxamate Resin", The International Journal of Applied Radiation and Isotopes vol. 34, Jun. 1983, United Kingdom, pp. 883-886.
Hider et al., "Chemistry and Biology of Siderophores", Natural Product Reports 27, 2010, United Kingdom, pp. 637-657.
Hodgkinson et al., "Oxalic Acid Metabolism in Man: A Review", Calcified Tissue Research vol. 2, Dec. 1968, Germany, pp. 115-132.
Hoffbrand, "Iron Chelation Therapy: Past, Present, and Future Prospects", The European Journal of Clinical & Medical Oncology vol. 2, 2010, United Kingdom, pp. 1-5.
Horwitz et al., "Chemical Separations for Super-Heavy Element Searches in Irradiated Uranium Targets", Journal of Inorganic and Nuclear Chemistry vol. 37, 1975, United Kingdom, pp. 425-434.
Horwitz et al., "Purification of Radionuclides for Nuclear Medicine: The Multicolumn Selectivity Inversion Generator Concept", Czechoslovak Journal of Physics vol. 53, Jan. 2003, United States, pp. A713-A716.

Iwata et al., "Comparative Study of Specific Activity of [11C]Methyl Iodide: A Search for the Source of Carrier Carbon", Applied Radiation and Isotopes vol. 39, 1988, United Kingdom, pp. 1-7.
Joshi et al., "Antioxidant Activity and Free Radical Scavenging Reactions of Gentisic Acid: In-Vitro and Pulse Radiolysis Studies", Free Radical Research vol. 46, Jan. 2012, United Kingdom, pp. 11-20.
Kandil et al., "A Comparative Study on the Separation of Radiozirconium via Ion-Exchange and Eolvent Extraction Techniques, with Particular Reference to the Production of 88Zr and 89Zr in Proton . . . ", Journal of Radioanalytical and Nuclear Chemistry vol. 274, Oct. 2007, Hungary, pp. 45-52.
Keliher et al., "89Zr-Labeled Dextran Nanoparticles Allow in Vivo Macrophage Imaging", Bioconjugate Chemistry vol. 22, 2011, United States, pp. 2383-2389.
Kim et al., "Ion Exchange in Aqueous and in Aqueous-Organic Solvents, Part I. Anion-Exchange Behaviour of Zr, Nb, Ta and Pa in Aqueous HCl-HF and in HCl-HF-Organic Solvent", Analytica Chimica Acta vol. 64, Mar. 1973, The Netherlands, pp. 29-43.
Kiss et al., "Metal-Binding Ability of Desferrioxamine B", Journal of Inclusion Phenomena and Molecular Recognition in Chemistry vol. 32, Nov. 1998, The Netherlands, pp. 385-403.
Koulouris et al., "Pre-Concentration of Actinoids from Waters: A Comparison of Various Sorbents", Applied Radiation and Isotopes vol. 53, Issues 1-2, Jul. 2000, United Kingdom, pp. 279-287.
Koulouris, "Dynamic Studies on Sorption Characteristics of 226Ra on Manganese Dioxide", Journal of Radioanalytical and Nuclear Chemistry vol. 193, Jun. 1995, Hungary, pp. 269-279.
Kraus et al., "Anion Exchange Studies. I. Separation of Zirconium and Niobium in HCl-HF Mixtures", Journal of the American Chemical Society vol. 73, Jan. 1951, United States, pp. 9-13.
Kruft et al., "Quantum Mechanical Investigation of Aqueous Desferrioxamine B Metal Complexes: Trends in Structure, Binding, and Infrared Spectroscopy", Journal of Inorganic Biochemistry vol. 129, Dec. 2013, United States, pp. 150-161.
Lee et al., "Study on the Separation of Carrier-Free Yttrium-90 from Strontium-90 Isotopes", Isotopenpraxis Isotopes in Environmental and Health Studies vol. 27, 1991, Germany, pp. 269-273.
Lehto et al., "Radiochemistry of the 4d-Transition Metals", Chapter 9 of Chemistry and Analysis of Radionuclides, Wiley-VCH Verlag GmbH & Co. KGaA, Weinheim, 2010, Germany, pp. 139-161.
Link et al., "89Zr for Antibody Labeling and Positron Emission Tomography", Journal of Labelled Compounds and Radiopharmaceuticals 23, 1986, Netherlands, pp. 1297-1298.
Link et al., "A Simple Thick Target for Production of 89Zr using an 11 MeV Cyclotron", Applied Radiation and Isotopes vol. 122, Apr. 2017, United Kingdom, pp. 211-214.
McAlister et al., "Automated Two Column Generator Systems for Medical Radionuclides", Applied Radiation and Isotopes vol. 67, Nov. 2009, United Kingdom, pp. 1985-1991.
Mishra et al., "Extraction of Zirconium(IV) from HCl Solutions by Mixtures of Aliquat-336 and Alamine-336 with TBP", Journal of Radioanalytical and Nuclear Chemistry vol. 134, 1989, Netherlands, pp. 259-264.
Mitsubishi Chemical Industries Limited, "Ion Exchange Selectivity", Diaion Manual of Ion Exchange Resins vol. 2, Mitsubishi Chemical Industries Limited, 1978, pp. 47-52.
Moon et al., "Preconcentration of Radium Isotopes from Natural Waters using MnO2 Resin", Applied Radiation and Isotopes vol. 59, 2003, United Kingdom, pp. 255-262.
Moore et al., "Adsorption of Iron by Anion Exchange Resins from Hydrochloric Acid Solutions", Journal of the American Chemical Society vol. 72, 1950, United States, pp. 5792-5793.
Moore et al., "Extraction of Radium from Natural Waters using Manganese-Impregnated Acrylic Fibers", Journal of Geophysical Research vol. 78, 1973, United States, pp. 8880-8886.
Morley et al., "An Automated Module for the Separation and Purification of Cyclotron-Produced 99mTcO4-", Nuclear Medicine and Biology vol. 39, May 2012, United States, pp. 551-559.
Mustafa et al., "Measurements and a Direct-Reaction-Plus-Hauser-Feshbach Analysis of 89Y(p,n)89Zr, 89Y(p,2n)88, and 89Y(p,pn)88Y Reactions up to 40 MeV", Physical Review C vol. 38, Oct. 1988, United States, pp. 1624-1637.

(56) References Cited

OTHER PUBLICATIONS

Nagatsu et al., "Fully Automated Production of Iodine-124 using a Vertical Beam", Applied Radiation and Isotopes vol. 69, Jan. 2011, United Kingdom, pp. 146-157.

Nayak et al., "Radioimmunoimaging with Longer-Lived Positron-Emitting Radionuclides: Potentials and Challenges", Bioconjugate Chemistry vol. 20, 2009, United States, pp. 825-841.

Nelson et al., "Ion Exchange Procedures: I. Cation Exchange in Concentrated HCl and HCLO4 Solutions", Journal of Chromatography A vol. 13, 1964, pp. 503-535.

O'Hara et al., "An Automated Flow System Incorporating In-Line Acid Dissolution of Bismuth Metal from a Cyclotron Irradiated Target Assembly for use in the Isolation of Astatine-211", Applied Radiation and Isotopes vol. 122, Apr. 2017, United Kingdom, pp. 202-210.

O'Hara et al., "Investigation of Magnetic Nanoparticles for the Rapid Extraction and Assay of Alpha-Emitting Radionuclides from Urine: Demonstration of a Novel Radiobioassay Method", Health Physics vol. 101, Aug. 2011, United States, pp. 196-208.

O'Hara et al., "Optimized Anion Exchange Column Isolation of Zirconium-89 (89Zr) from Yttrium Cyclotron Target: Method Development and Implementation on an Automated Fluidic Platform", Journal of Chromatography A, vol. 1545, 2018, The Netherlands, pp. 48-58.

O'Hara et al., "Tandem Column Isolation of Zirconium-89 from Cyclotron Bombarded Yttrium Targets Using an Automated Fluidic Platform: Anion Exchange to Hydroxamate Resin Columns", Journal of Chromatography A, vol. 1567, 2018, The Netherlands, pp. 37-46.

Omara et al., "Proton Induced Reactions on 89Y with Particular Reference to the Production of the Medically Interesting Radionuclide 89Zr", Radiochimica Acta vol. 97, Issue 9, 2009, Germany, pp. 467-471.

Queern et al., "Production of Zr-89 Using Sputtered Yttrium Coin Targets", Nuclear Medicine and Biology vol. 50, Jul. 2017, United States, pp. 11-16.

Severin et al., "89Zr Radiochemistry for Positron Emission Tomography", Medicinal Chemistry vol. 7, Sep. 2011, United States, pp. 389-394.

Skudaev et al., "Oxidation of Hydrogen Chloride with Hydrogen Peroxide in Aqueous Solution", Russian Journal of Applied Chemistry vol. 81, Jan. 2008, Russian Federation, pp. 14-16.

Strelow, "Distribution Coefficients and Ion Exchange Behavior of 46 Elements with a Macroreticular Cation Exchange Resin in Hydrochloric Acid", Analytical Chemistry vol. 56, 1984, United States, pp. 1053-1056.

Tang et al., "A Simple and Convenient Method for Production of 89Zr with High Purity", Applied Radiation and Isotopes vol. 118, Dec. 2016, United Kingdom, pp. 326-330.

Valentine et al., "Removing Radium by Adding Preformed Hydrous Manganese Oxides", Journal of the American Water Works Association vol. 82, 1990, pp. 66-71.

Varga, "Preparation and Characterization of Manganese Dioxide Impregnated Resin for Radionuclide Pre-Concentration", Applied Radiation and Isotopes vol. 65, Issue 10, Oct. 2007, United Kingdom, pp. 1095-1100.

Walther et al., "Implementation of 89Zr Production and In Vivo Imaging of B-Cells in Mice with 89Zr-Labeled Anti-B-Cell Antibodies by Small Animal PET/CT", Applied Radiation and Isotopes vol. 69, Issue 6, Jun. 2011, United Kingdom, pp. 852-857.

Warner et al., "Manganese Doping of Magnetic Iron Oxide Nanoparticles: Tailoring Surface Reactivity for a Regenerable Heavy Metal Sorbent", Langmuir vol. 28, 2012, United States, pp. 3931-3937.

Zhang et al., "PET Tracers Based on Zirconium-89", Current Radiopharmaceuticals vol. 4, 2011, United States, pp. 131-139.

Raymond et al., "Complexation of Iron by Siderophores: A Review of their Solution and Structural Chemistry and Biological Function", Structural Chemistry, 1984, United States, pp. 49-102.

Small, "The Chromatographic Process", Chapter 2, Section 2.3.1, equation 2.1, Ion Chromatography, Springer Science+Business Media, New York, 1989, United States, p. 13.

* cited by examiner

SYSTEM AND PROCESS FOR PRODUCTION OF ISOTOPES AND ISOTOPE COMPOSITIONS

CROSS REFERENCE TO RELATED APPLICATION

This application claims priority to U.S. Patent Application Ser. No. 62/410,303 filed Oct. 19, 2016, entitled "System and Process for Production of Labeling-Grade Zirconium-89", the entirety of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

TECHNICAL FIELD

The present disclosure relates to materials, methods, and compositions for use in isotope purification and/or PET isotope production. Particular embodiments provide materials, methods, and compositions for use in $^{89}$Zr purification and PET production.

BACKGROUND

Availability of longer-lived positron emitters has made PET-based imaging of tumors possible by radiolabeling monoclonal antibodies (mAbs), mAb fragments and aptamers, a process referred to as immuno-PET. Immuno-PET combines the high sensitivity and spatial resolution of PET imaging with the antigen specificity of mAbs. Use of $^{89}$Zr is gaining tremendous interest in Europe and the U.S. as an immunoPET diagnostic isotope due to its ease of production using monoisotopic (natural) yttrium targets and moderate-to-low energy medical cyclotrons. The long half-life of $^{89}$Zr ($T_{1/2}$=78.4 hr) also enables the potential for off-site isotope production and distribution and for opportunities in new and emerging medical modalities.

Given the high cost of specialty proteins used in immuno-PET diagnostic imaging, it is desirable that binding yields onto these proteins be as high as possible. Another drawback of existing $^{89}$Zr purification processing is the high dose rates to personnel that can occur from process scale-up. Accordingly, new processes are needed that address the residual metal contamination for medical applications and personnel dose rates. Embodiments described in the present disclosure address these needs.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY OF THE DISCLOSURE

Methods for purifying $^{89}$Zr are provided with the methods including: loading a hydroxamate resin with a loading solution comprising HCl and $^{89}$Zr; and eluting the $^{89}$Zr from the resin using an oxalic acid solution having molarity of less than 1. Useful eluting solutions are provided that can include $^{89}$Zr and less than 1 M oxalic acid.

Methods for purifying $^{89}$Zr can also include: preparing a loading solution comprising $^{89}$Zr and HCl; exposing the loading solution to an ion exchange resin; and eluting the $^{89}$Zr from resin using an HCl solution having a molarity greater than 0.3.

Methods for purifying $^{89}$Zr can also include: loading a first resin with a first loading solution comprising $^{89}$Zr; eluting the $^{89}$Zr from the first resin using a first eluting solution; loading a second resin with a second loading solution comprising $^{89}$Zr; and eluting the $^{89}$Zr from the second resin using a second eluting solution.

$^{89}$Zr compositions are provided that may have bindable metal concentration ($[M_B]$) less than 169 nmole·g$^{-1}$ or effective specific activity (ESA) of greater than 800 Ci·mmole$^{-1}$.

Isotope compositions are provided that can include: a radio isotope and a nanoparticle.

Other isotope compositions can include: a radio isotope; a nanoparticle; and a macromolecule.

Methods for radio labeling monoclonal antibodies are provided that can include: preparing a binding conjugate by exposing a ligand to a solution of $^{89}$Zr and less than 1 M oxalic acid.

Methods for radio labeling monoclonal antibodies are also provided that can include: exposing monoclonal antibodies to a solution of $^{89}$Zr having a have bindable metal concentration ($[M_B]$) less than 169 nmole·g$^{-1}$ or effective specific activity (ESA) of greater than 800 Ci·mmole$^{-1}$.

DRAWINGS

Embodiments of the disclosure are described below with reference to the following accompanying drawings.

FIG. 1 is a depiction of resin loading and elution according to embodiments of the disclosure.

FIG. 2 is a fluidic system configured for the hydroxamate column separation of $^{89}$Zr from irradiated Y metal targets. Labels: Syringe Pump w/ 8-port distribution valve, 2-position Valve, Column, Detection coil, Fraction Collector, Reaction Flask, Peristaltic Pump, and in-line Filter. Blocked port is indicated by "x"; outward arrows on SP and V indicate lines to waste. V is shown in position "1".

Figure 5:
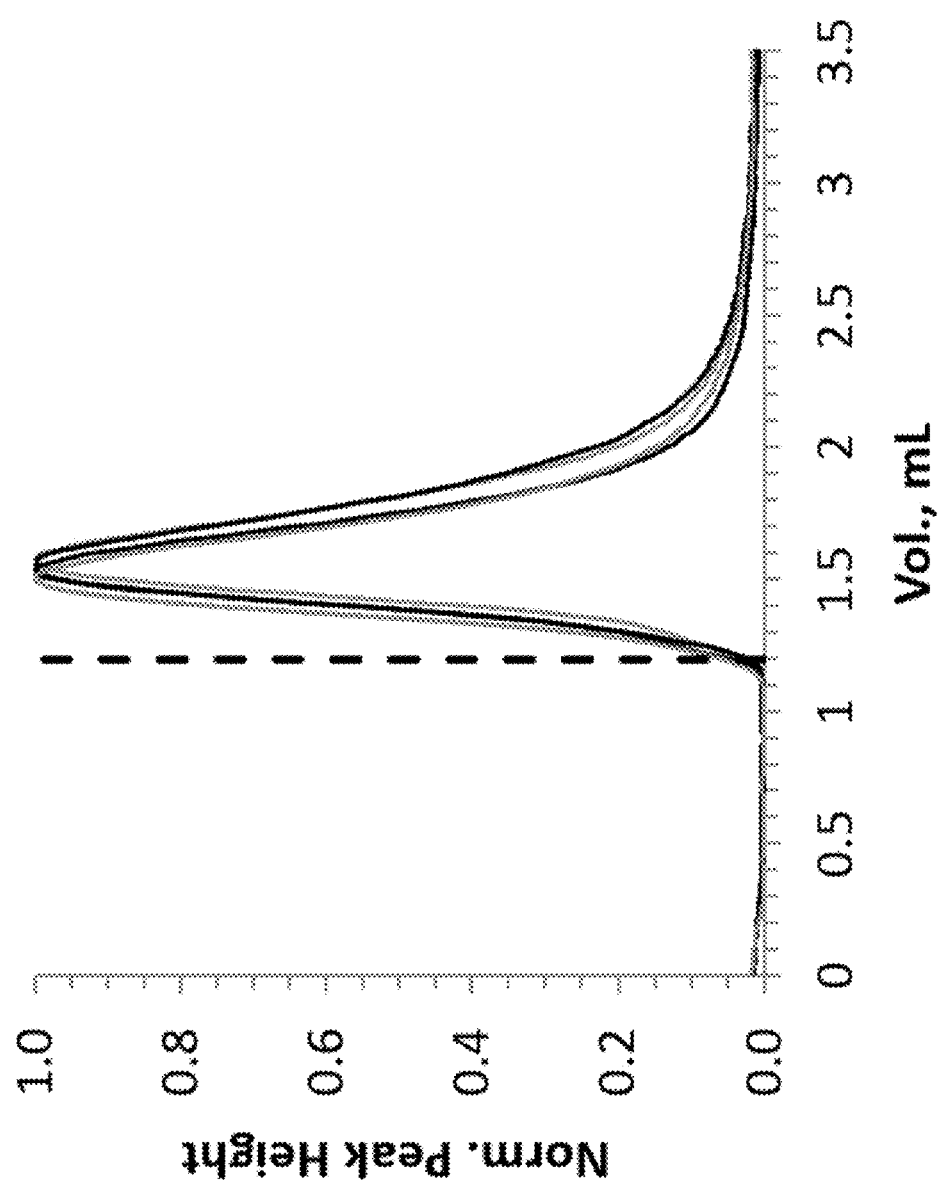

FIG. 5 is a graph of four replicate elution profiles for $^{89}$Zr from a hydroxamate column (100 mg) using 0.8 M $H_2C_2O_4$. Peak heights are normalized to each peak maxima. Time zero is set to the delivery of the eluent solution to the evacuated column delivery line. Vertical line represents the reference point (1.21±0.03 mL) for evaluation of peak parameters.

Figure 6:
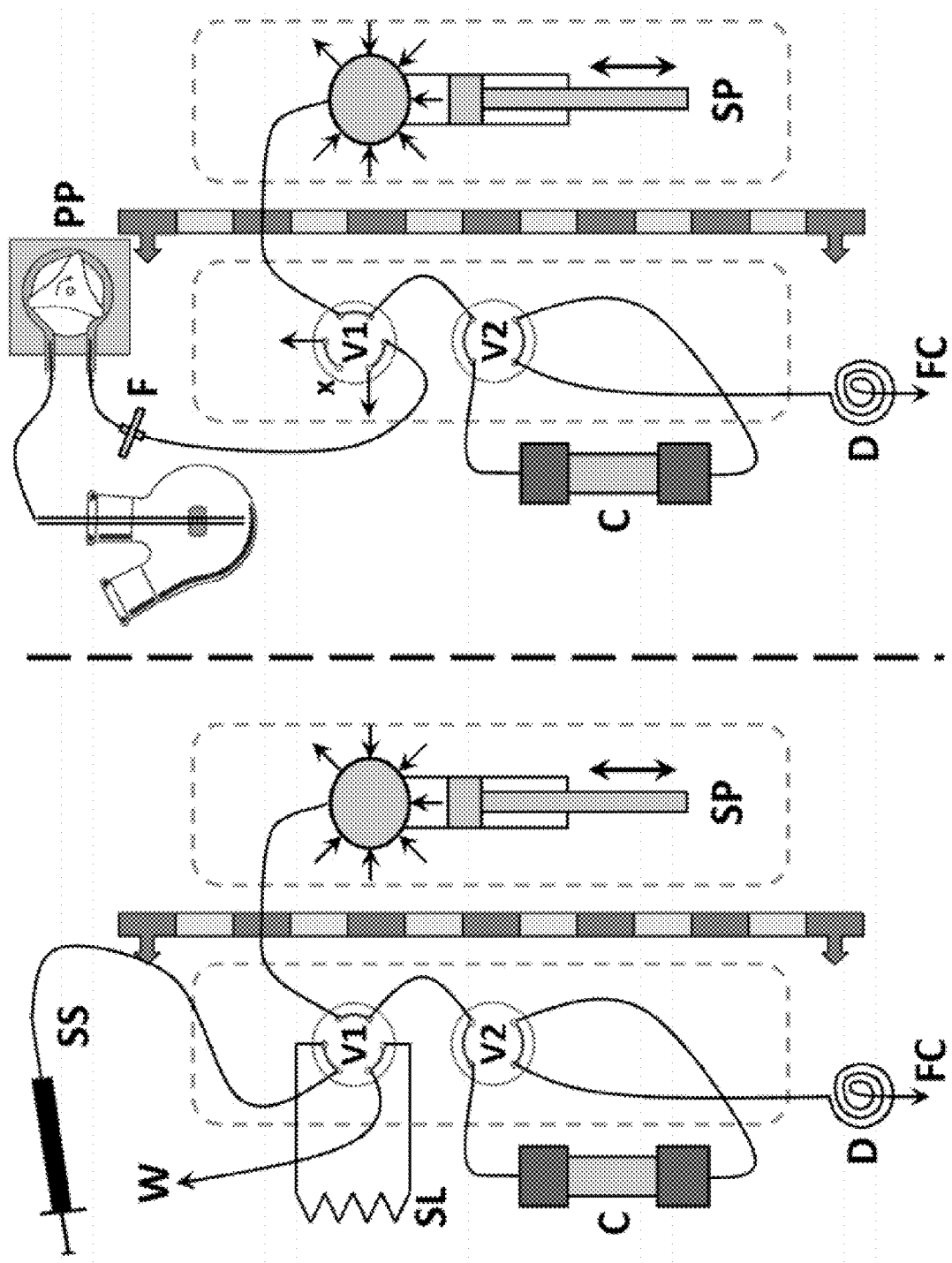

FIG. 6 depicts schematics of fluidic system configurations for the separation of $^{89}$Zr from yttrium target. (Left) System configured with a sample loop. (Right) The column receives the dissolved Y target from the flask via a peristaltic pump. Labels: Syringe Pump w/ 8-port distribution valve, 2-position Valve, Sample Loop, Column, Detection coil, Fraction Collector, Sample Syringe, Peristaltic Pump, and in-line Filter. Blocked port is indicated by "x"; outward arrows on SP and V1 indicate lines to waste. V1 and V2 are shown in position "1".

Figure 7:
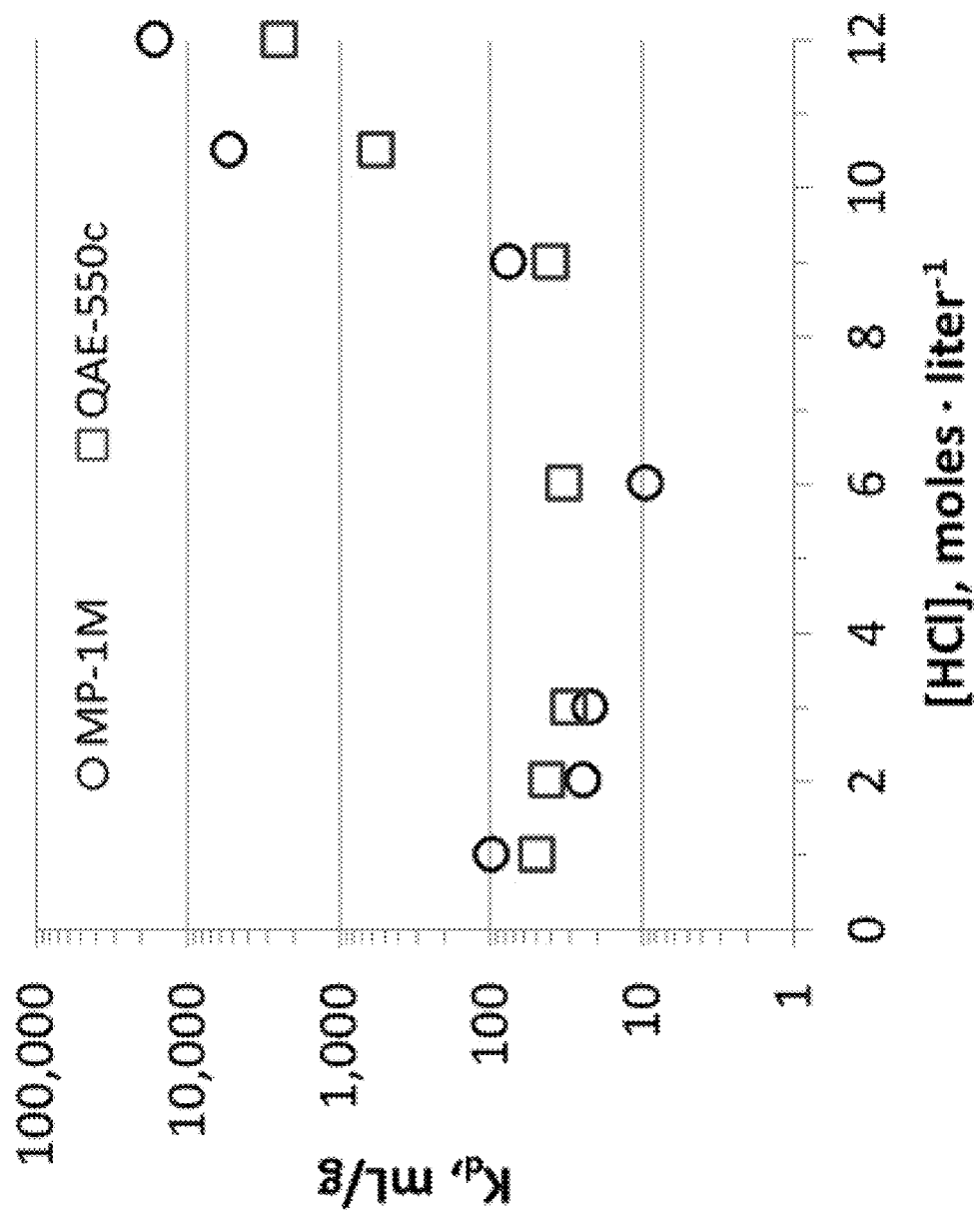

FIG. 7 depicts distribution coefficient ($K_d$) values for $^{88}$Zr tracer as a function of HCl concentration for two strongly basic anion exchange resins.

Figure 8:
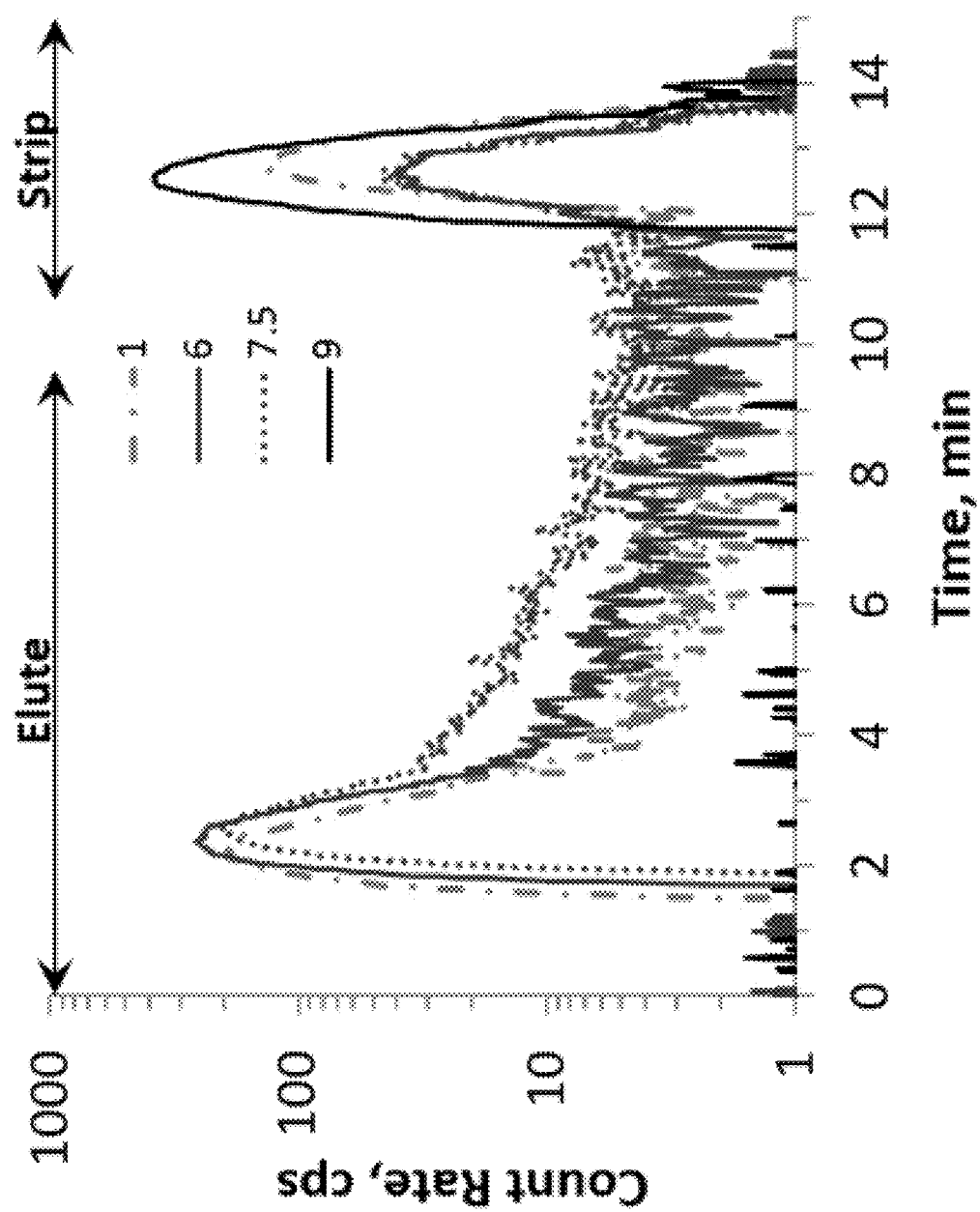

FIG. 8 is an overlay of radiochromatograms showing several radio-Zr elutions (7.5 mL) with varying concentrations of HCl, followed by column strip, from an MP-1M strongly basic anion exchange resin column. The time between arrows represents fluid delivery delay during syringe pump reloading operations. Legend indicates HCl eluent concentrations, in moles·liter$^{-1}$.

Figure 9:
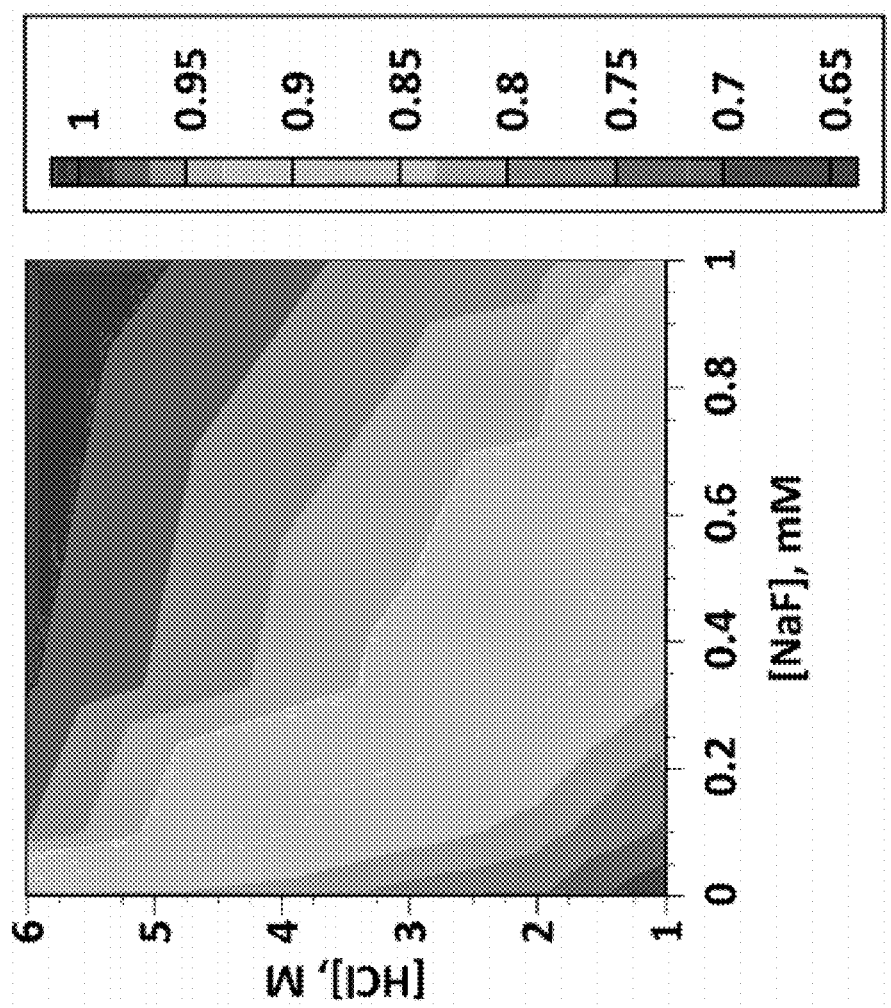

FIG. 9 is a contour plot of the radio-Zr recovery fractions observed during a 7.5 mL eluent delivery to the MP-1M column following load/wash of radio-Zr in concentrated (conc.) HCl. Optimal $^{88}$Zr recovery fraction was observed between 6 M HCl+(0.33-1.0) mM NaF. (Contour lines calculated by DeltaGraph v. 5.6.4).

Figure 10:
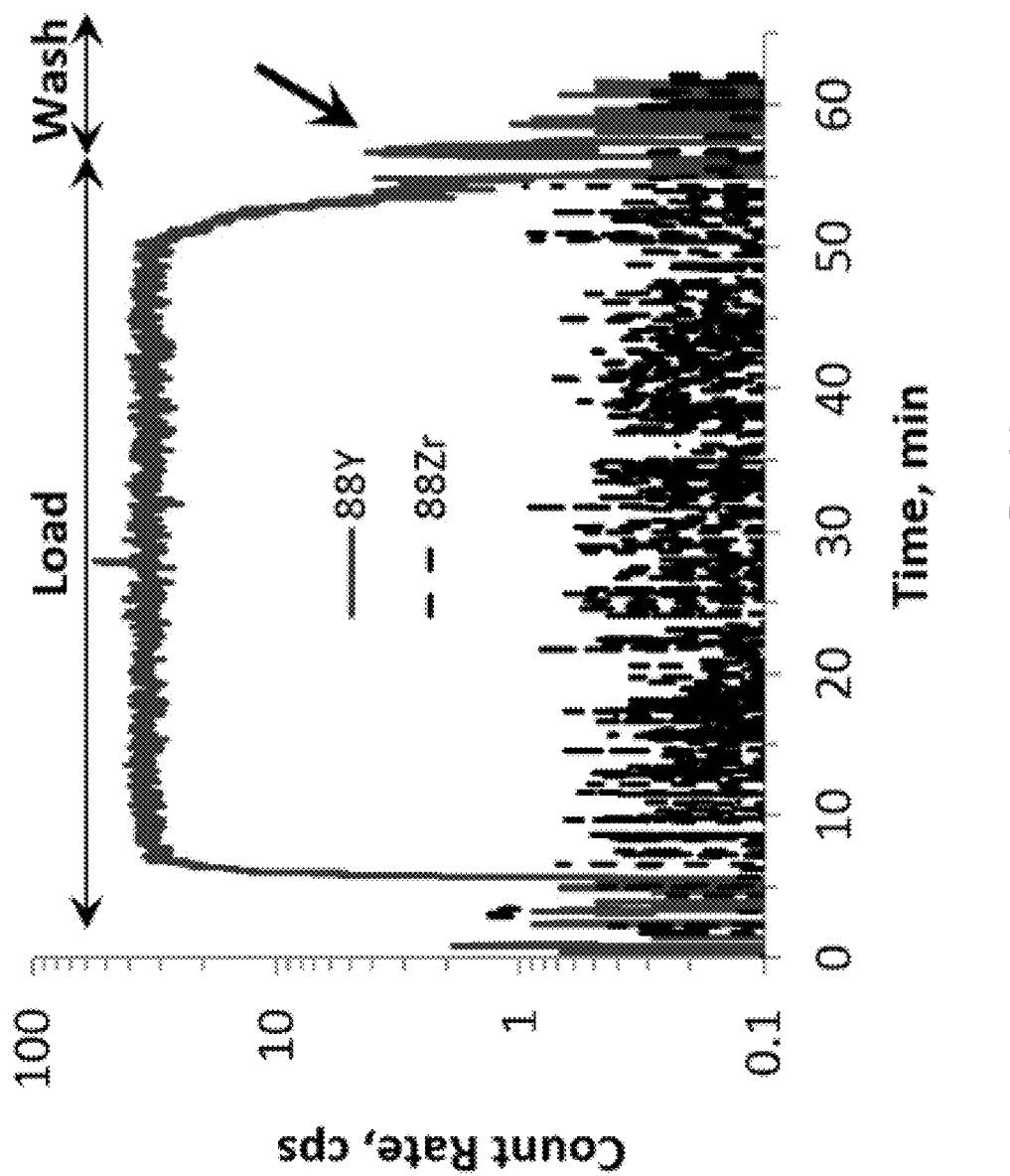

FIG. 10 is a load of simulated dissolved Y foil target (20 mL of 25 mg/mL Y) that was spiked with either $^{88}$Zr or $^{88}$Y radiotracers and delivered by peristaltic pump to the column (0.5 mL/min). Next, 5 mL column wash (conc. HCl) was delivered via syringe pump (0.75 mL/min). Arrow indicates a small peak resulting from removal of $^{88}$Y from droplets in the empty tubing and interstitial spaces of the column.

Figure 11:
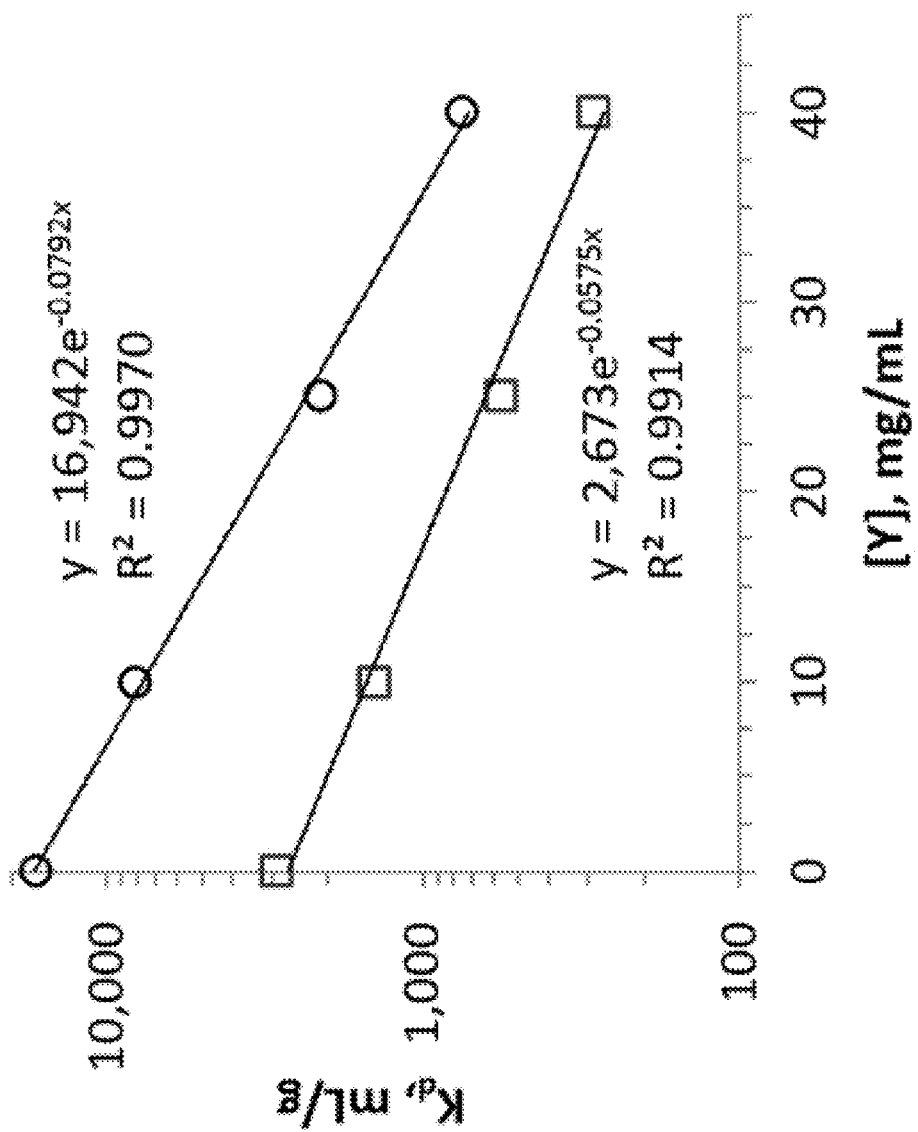

FIG. 11 depicts distribution coefficient ($K_d$) values for radio-Zr on MP-1M (○) and QAE-550C (□) as a function of dissolved Y metal concentration in conc. HCl.

Figure 12:
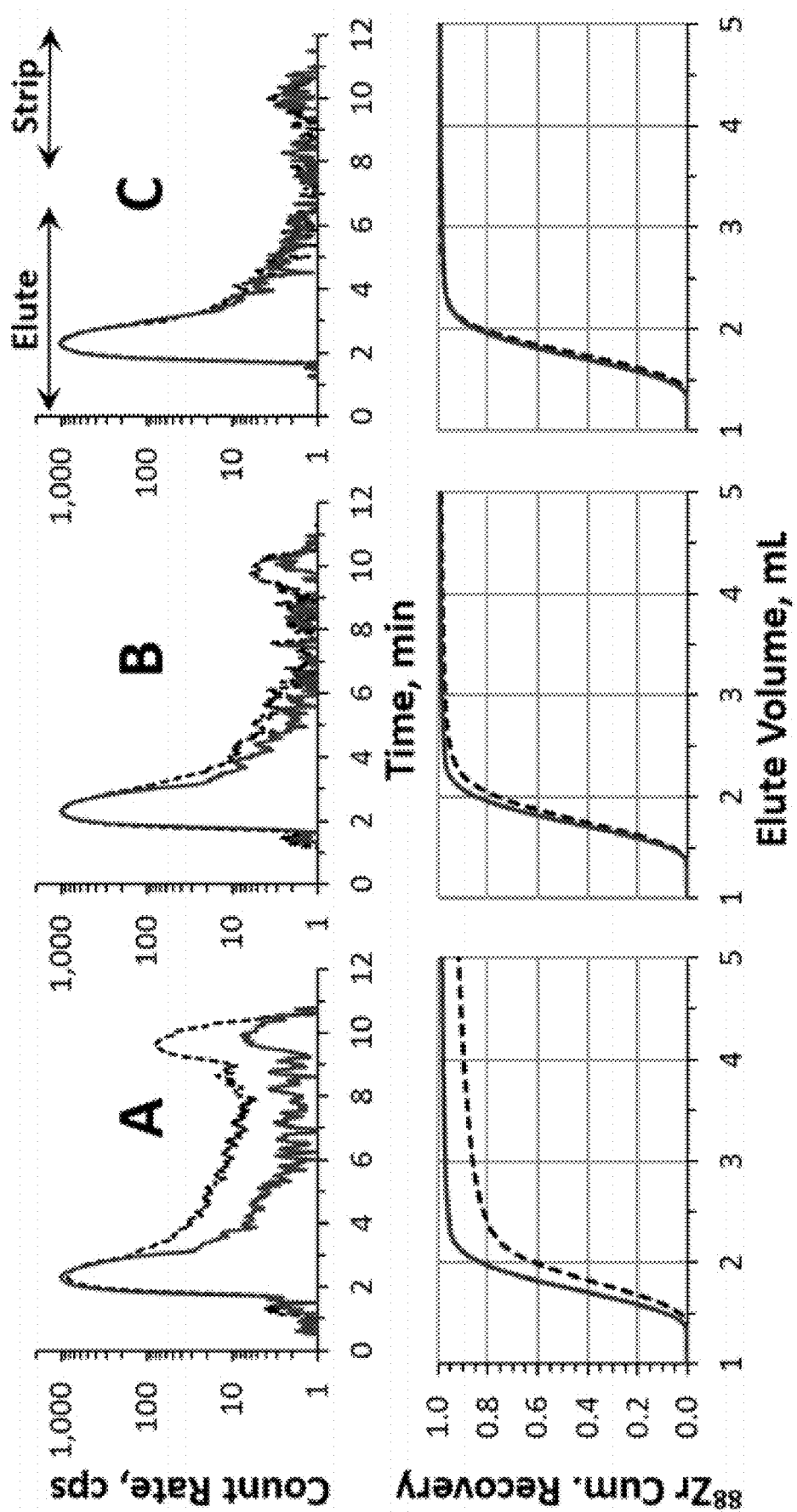

FIG. 12 depicts radiochromatograms; (Top Row) Radiochromatogram pairs showing the elution (5 mL) and strip traces of $^{88}$Zr tracer following load/wash from 0.5 g dissolved Y metal (25 mg/mL). Elute and strip reagents are delivered in forward flow (- - -) and reverse flow (▬) directions; eluent solutions are (A) 6 M HCl, (B) 6 M HCl+0.33 mM NaF, and (C) 6 M HCl+1.0 mM NaF. (Bottom Row) Corresponding cumulative recovery of $^{88}$Zr tracer across the 5 mL elution volume.

Figure 13:
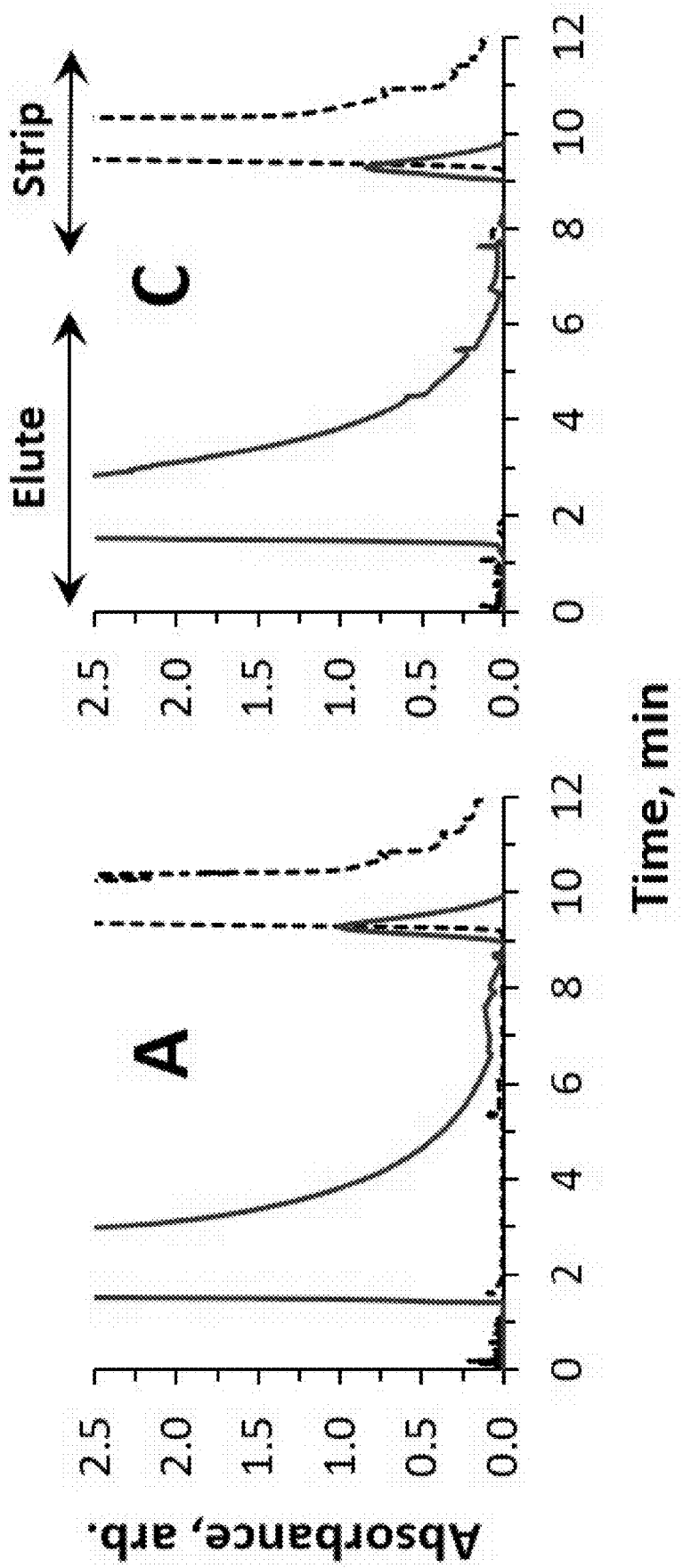

FIG. 13 depicts on-line absorptivity traces of ferric chloride across the MP-1M column elute and strip cycles (360 nm). (A) FF (- - -) and RF (▬) observed during a 6 M HC elution. (C) FF (- - -) and RF (▬) observed during a 6 M HCl+1 mM NaF elution. The fluid delivery methods are identical to those utilized for $^{88}$Zr tracer experiments in FIG. 12, conditions A and C.

Figure 14:
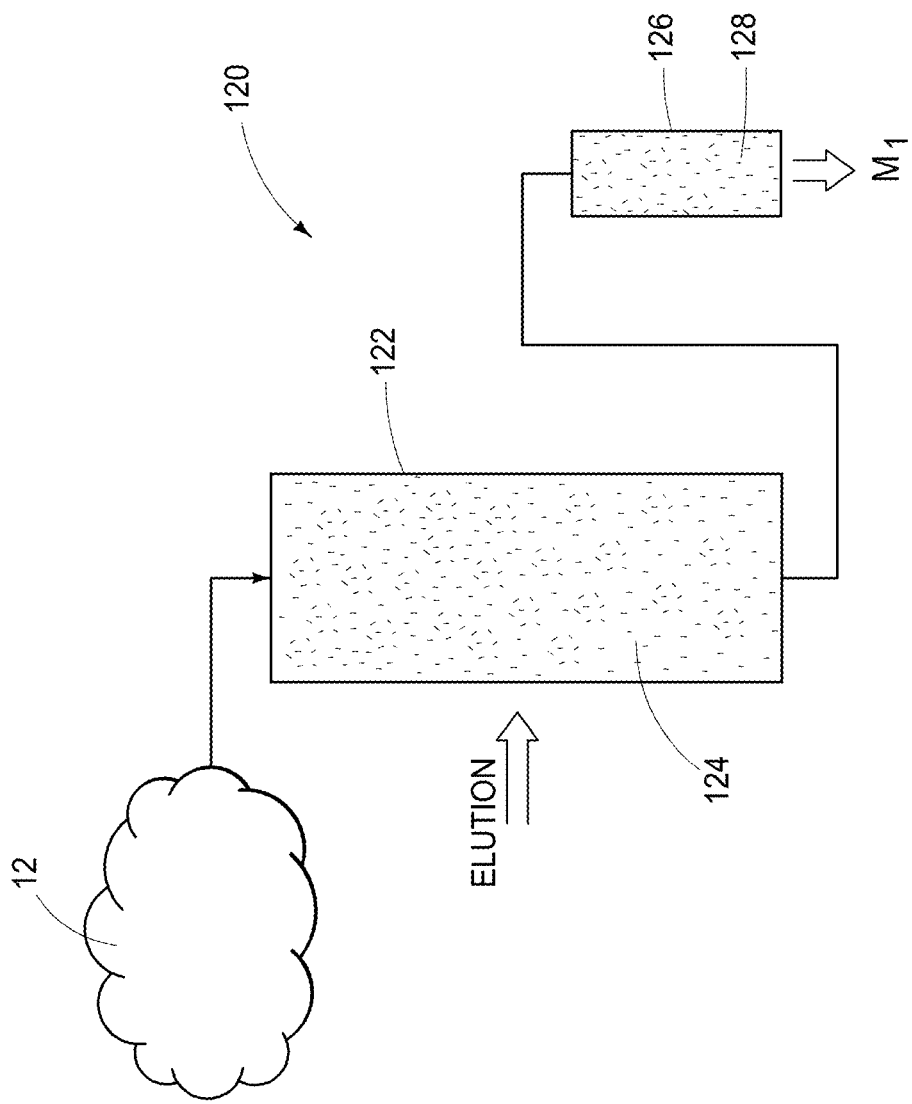

FIG. 14 is a depiction of a dual column purification system according to an embodiment of the disclosure.

Figure 15:
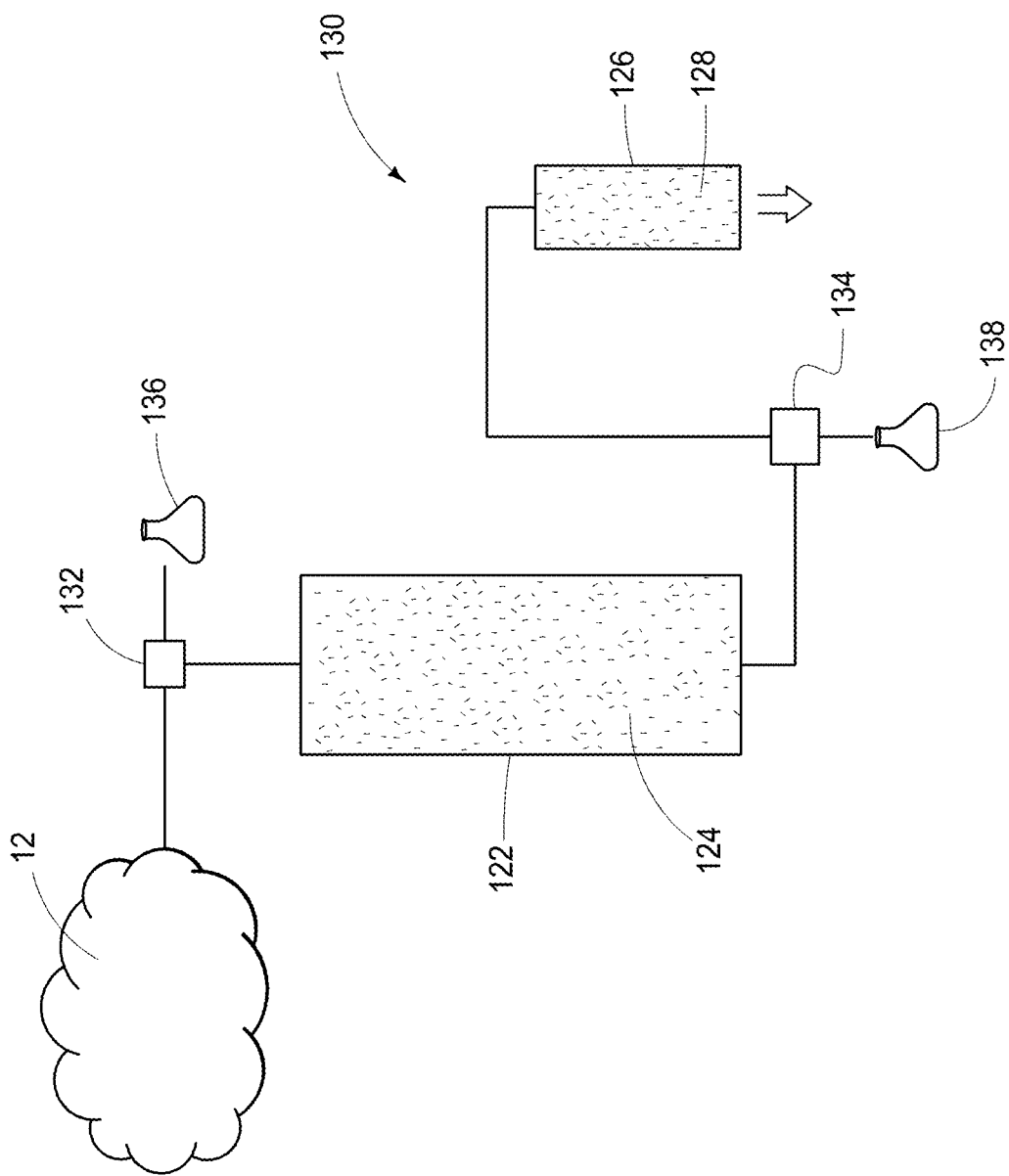

FIG. 15 is a depiction of another dual column purification system according to an embodiment of the disclosure.

Figure 16:
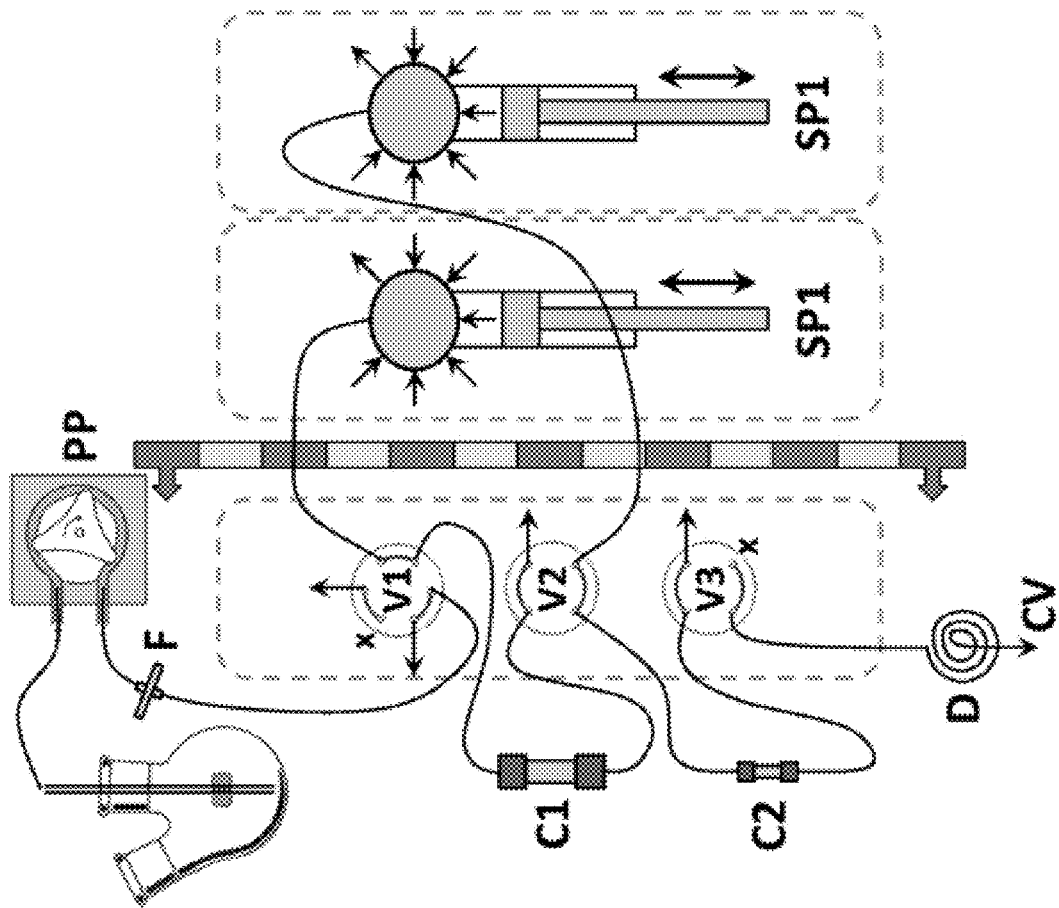
Figure 16:
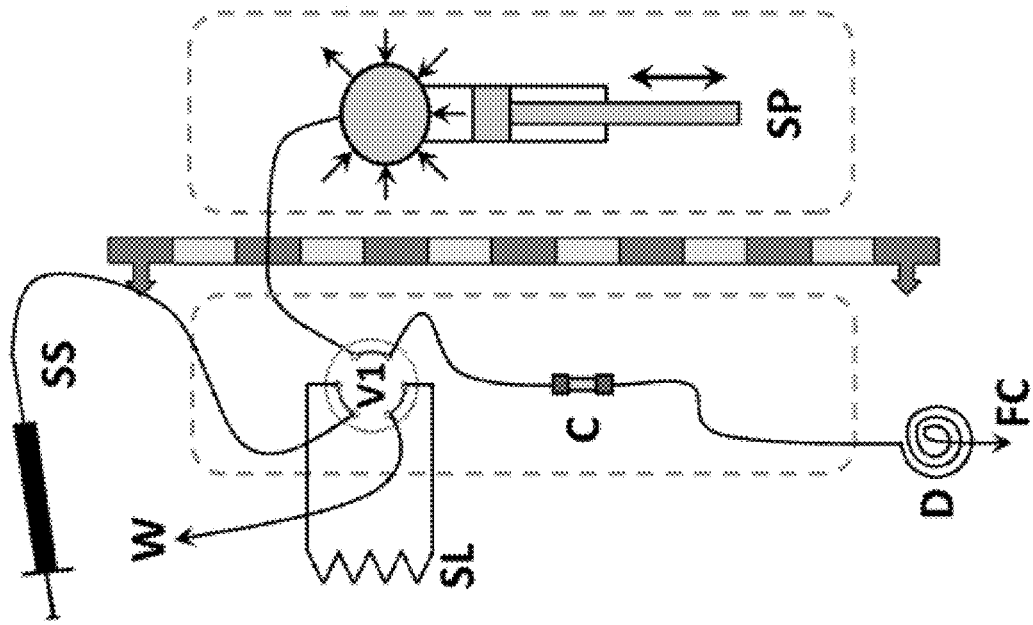

FIG. 16 depicts purification systems according to an embodiment of the disclosure: (Left) Fluidic system to evaluate the performance of the secondary column in isolation of the primary column. (Right) Fluidic system configured for the tandem column separation of $^{89}$Zr from irradiated Y metal targets. The column receives the dissolved Y metal from the flask via a peristaltic pump. Labels: Syringe Pumps w/ 8-port distribution valves, 2-position Valves, Columns, Sample injection Syringe, Detection coil, Fraction Collector, $^{89}$Zr product Collection Vessel, Peristaltic Pump, and in-line Filter. Blocked ports are indicated by an "x"; arrows indicate lines to waste. Valves are shown in position "1".

Figure 17:
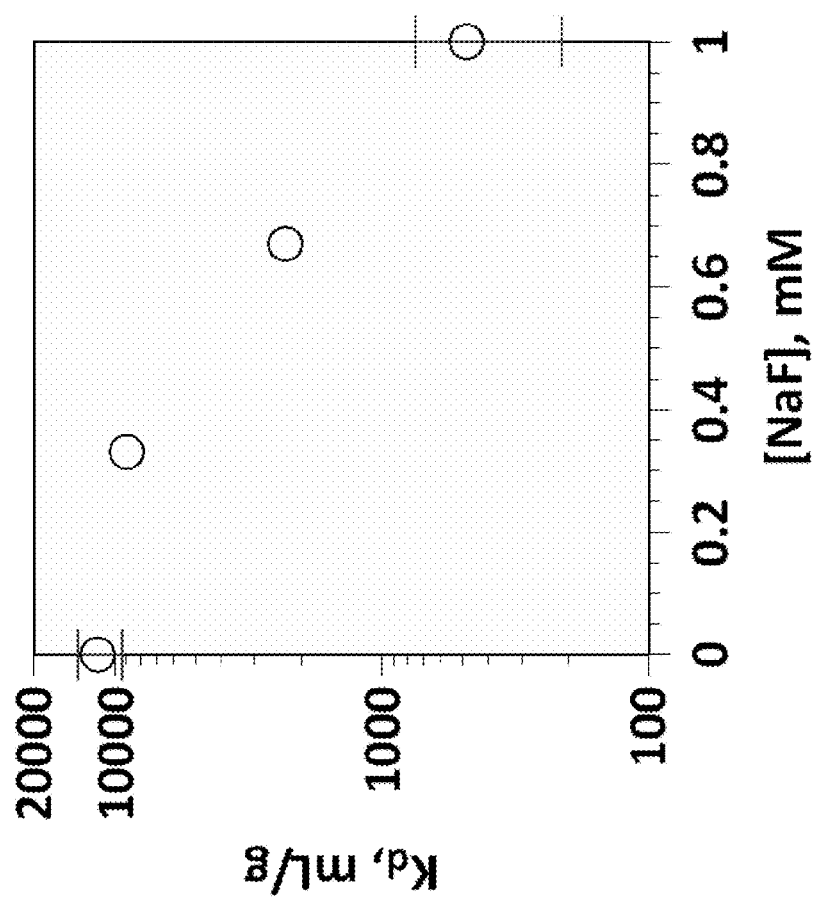

FIG. 17 depicts distribution coefficient ($K_d$) values for $^{88}$Zr tracer as a function of NaF concentration in 6 M HCl on hydroxamate resin.

Figure 18:
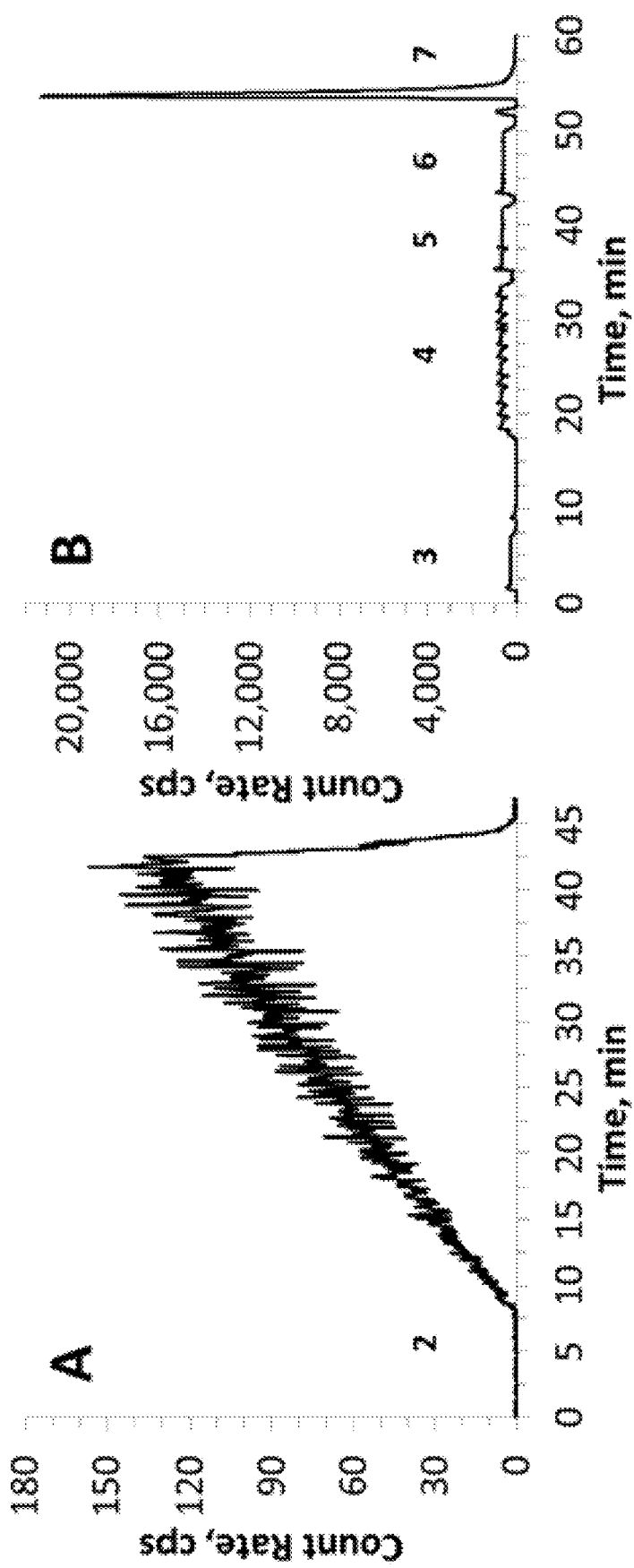

FIG. 18 depicts graphs of on-line detector traces of column effluents during a tandem column separation. (A) Loading $^{89}$Zr from dissolved irradiated Y target onto primary column. (B) Tandem column separation followed by $^{89}$Zr elution. Except for the $^{89}$Zr elution peak at (7), detected activity is from the sorbed $^{89}$Zr's continuous production of unretained $^{89m}$Y daughter.

Figure 19:
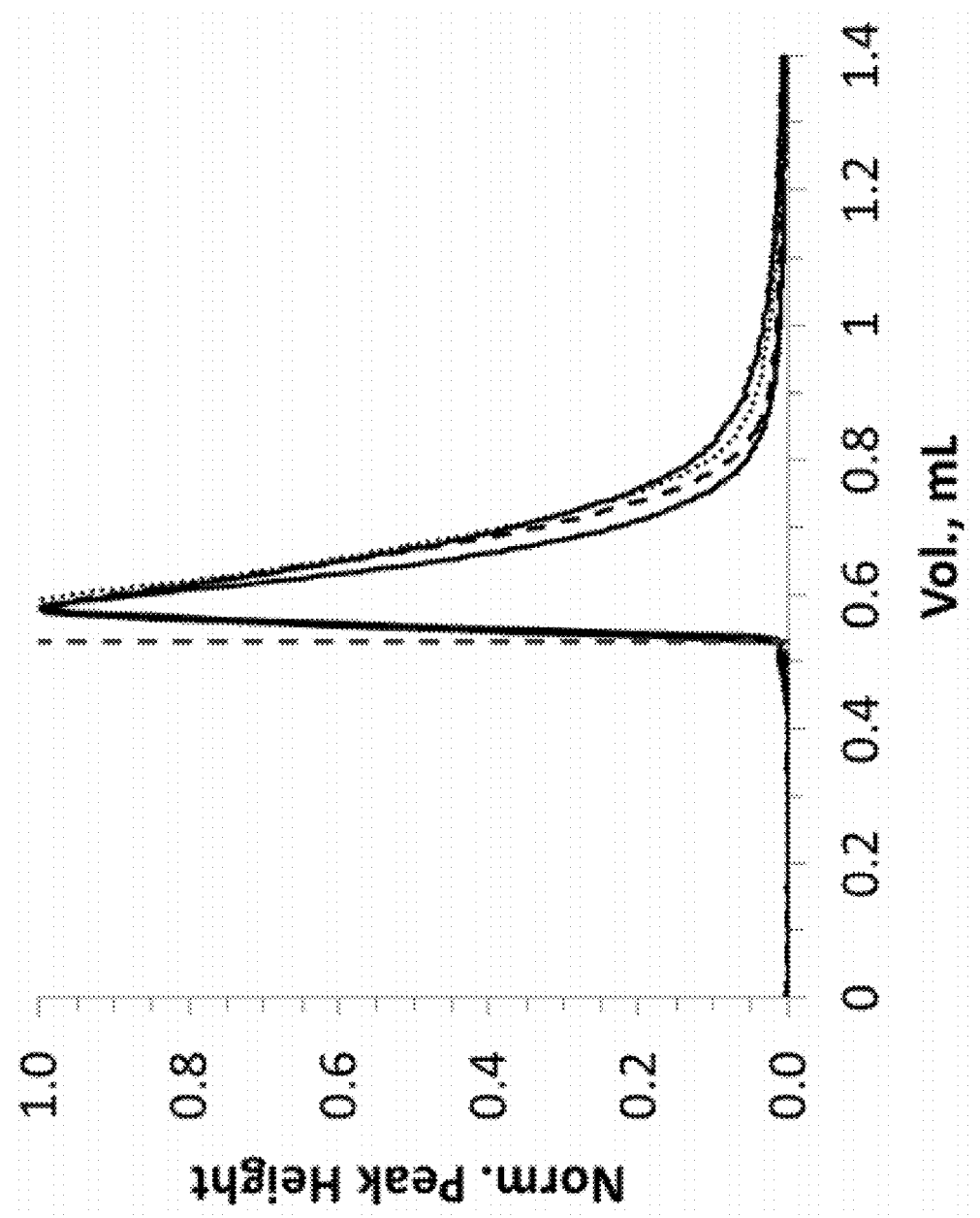

FIG. 19 depicts quadruplicate detector traces showing elution profiles for $^{89}$Zr from a hydroxamate microcolumn in 0.8 M $H_2C_2O_4$. Peak heights are normalized to the peak maxima for comparison. Vertical line is set at the elution start reference point of 0.536 mL.

Figure 20:
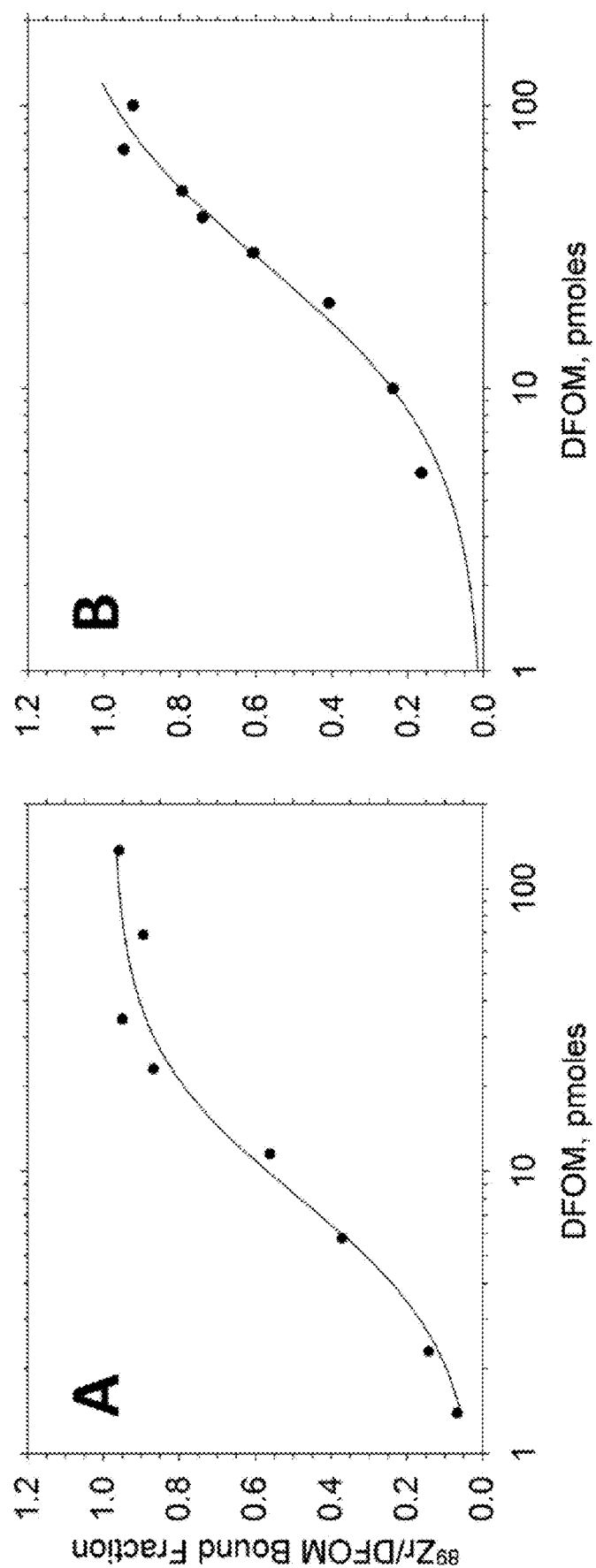

FIG. 20 depicts $^{89}$Zr binding fraction results on aminopropyl anion exchange cartridge plotted as a function of deferoxamine mesylate (Dfo-m) present in the transchelation solution in a Dfo-m titration experiment.

Figure 21:
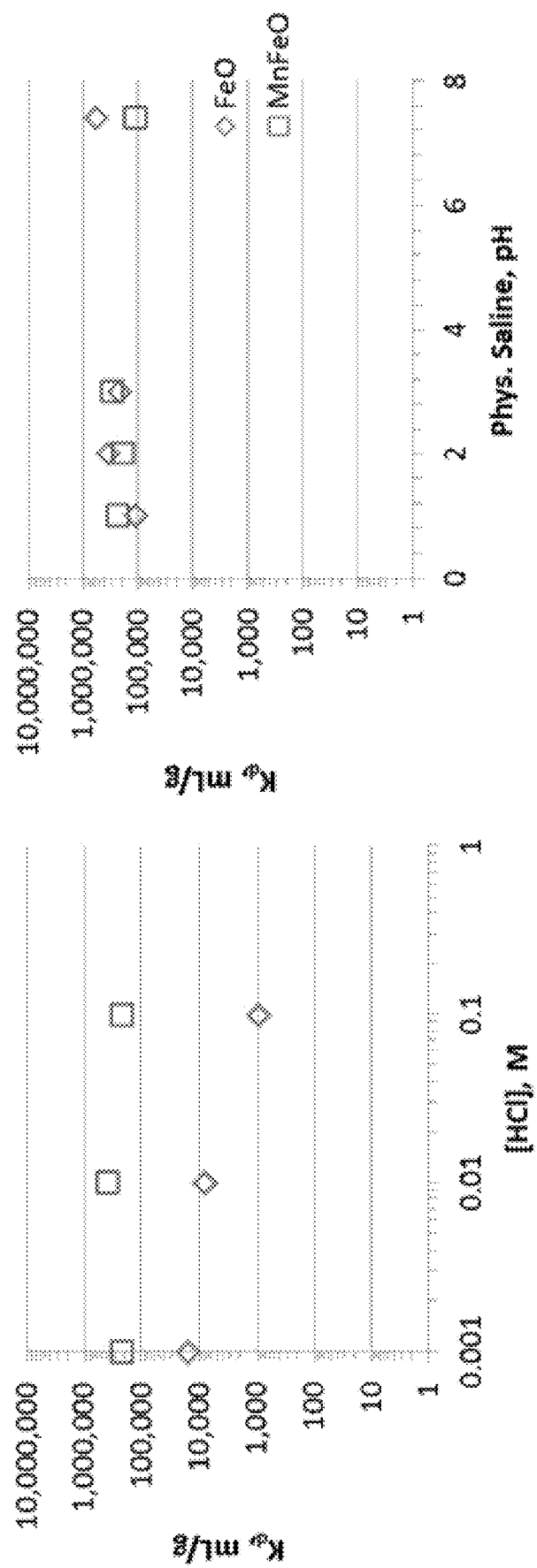

FIG. 21 depicts distribution coefficients ($K_d$) of $^{88}$Zr tracer onto $Fe_3O_4$ and Mn-doped $Fe_3O_4$ magnetic nanoparticles in varying concentrations of HCl (left) and pH-adjusted phosphate buffered saline (right).

Figure 22:
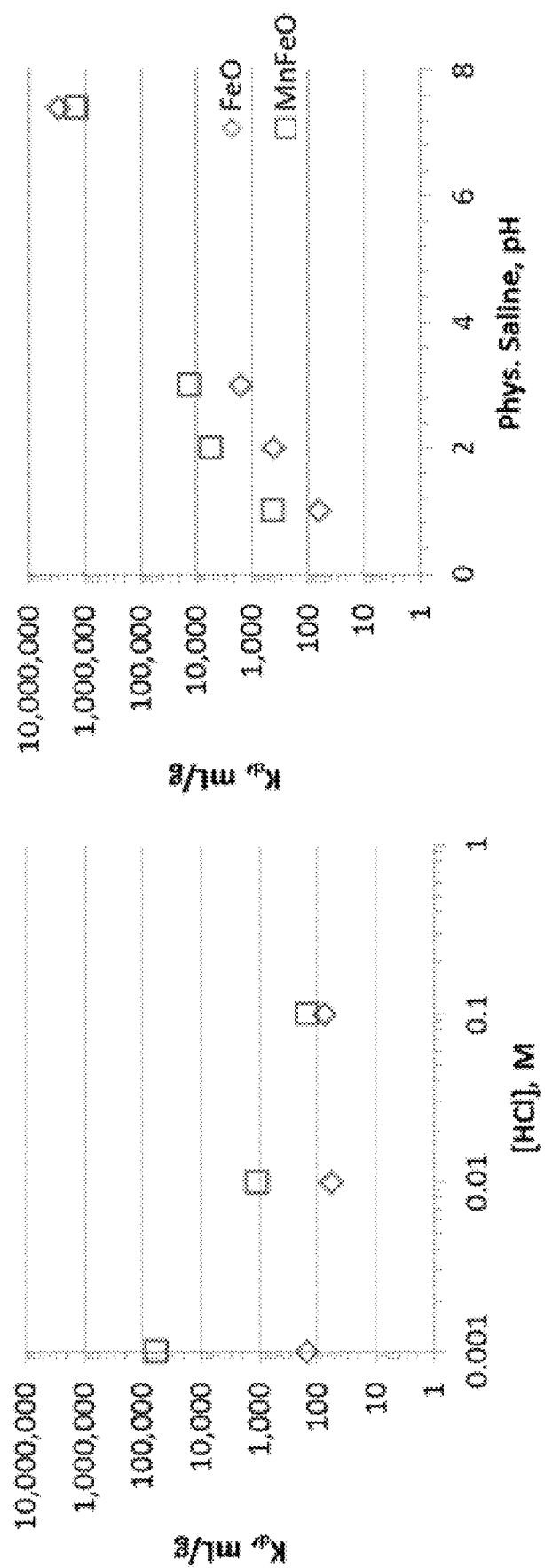

FIG. 22 depicts distribution coefficients ($K_d$) of $^{88}$Y tracer onto $Fe_3O_4$ and Mn-doped $Fe_3O_4$ magnetic nanoparticles in varying concentrations of HCl (left) and pH-adjusted phosphate buffered saline (right).

Figure 23:
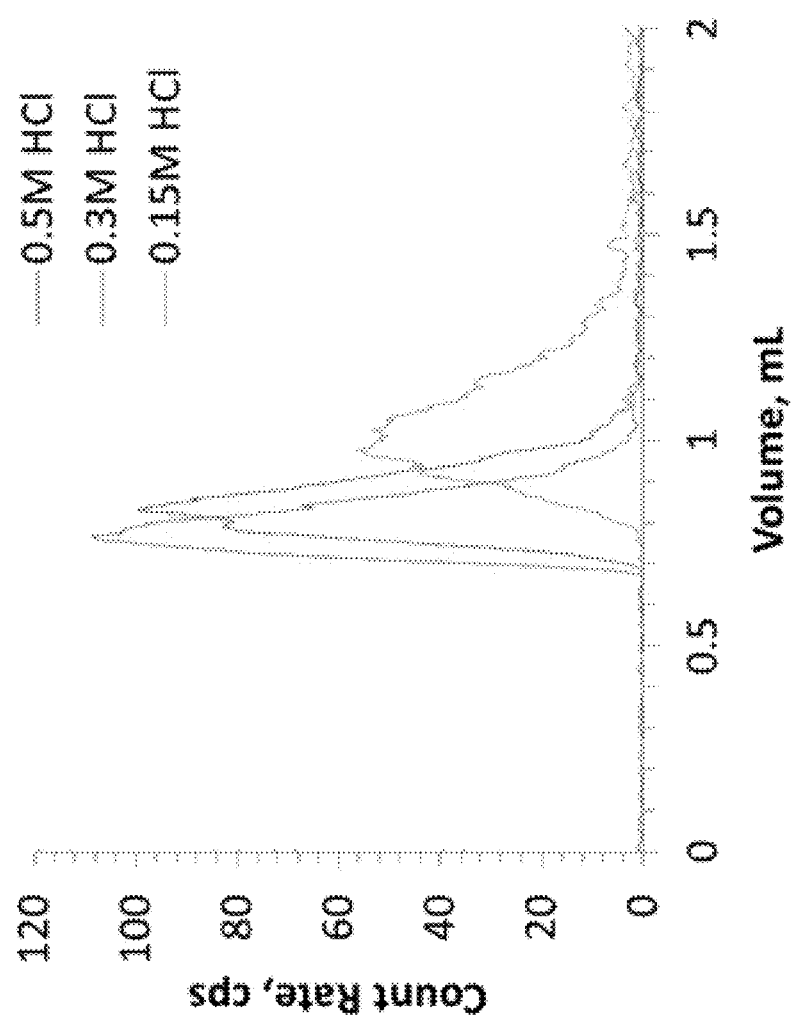

FIG. 23 depicts $^{88}$Zr chloride elution profiles from QAE-550C mini-column. $^{88}$Zr oxalate is loaded onto the column; column is converted to the formate form; then low concentrations of HCl are used to elute the $^{88}$Zr tracer as $ZrCl_4$.

DESCRIPTION

This disclosure is submitted in furtherance of the constitutional purposes of the U.S. Patent Laws "to promote the progress of science and useful arts" (Article 1, Section 8).

The materials, methods, and compositions of the present disclosure will be described with reference to accompanying FIGS. 1-23 as well as U.S. Provisional Patent Application Ser. No. 62/410,303 filed Oct. 19, 2016, entitled "System and Process for Production of Labeling-Grade Zirconium-89", the entirety of which is incorporated by reference herein.

Figure 1:
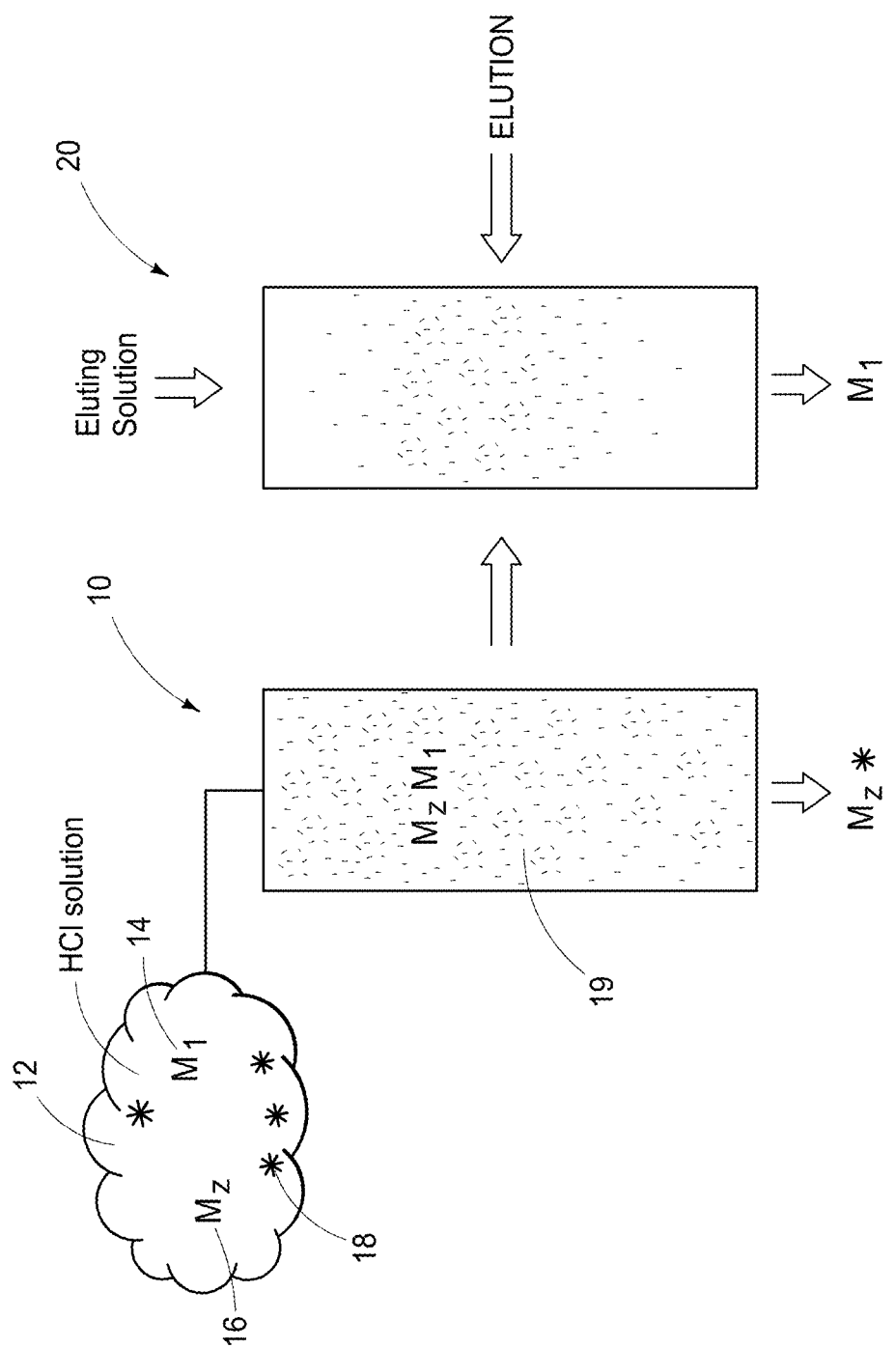

Referring first to FIG. 1, an example purification method is shown using a single resin. In the first instance, system 10 is loaded with material to be purified. Material 12 can include a mixture of materials, such as an isotope $M_1$ (14), contaminant metals $M_z$ (16) and other materials * (18). In accordance with example implementations, material 12 can be exposed to resin material 19.

In accordance with example implementations, methods for purifying the isotope $^{89}$Zr, can include loading a hydroxamate resin material, in a column, with a loading solution comprising HCl and $^{89}$Zr. This solution can be directly obtained with the dissolution of yttrium. Example irradiated yttrium can include, but is not limited to, cyclotron bombarded Y foil, for example. Some metals of the solution, $M_1$ and $M_z$, may be bound to the resin, and much of the remainder of the loaded solution removed from the resin.

In accordance with example implementations, the resin can be exposed to an eluting solution, in this case a solution of oxalic acid having a molarity less than 1. The oxalic acid solution ($H_2C_2O_4$) can be between 0.3 and less than 1 M, or 0.8 and less than 1 M. In accordance with example implementations, a solution can be obtained during elution in system 20 that includes $^{89}$Zr and less than 1 M oxalic acid. For example, this results in the need for less buffering agents to be added to the $^{89}$Zr product fraction prior to mAb labeling. In accordance with example implementations, eluted $^{89}$Zr product fractions demonstrated chemical recoveries from irradiated Y foil targets, with 1 mL product volumes yielding 89±2% of the elution peak activity and 84±2% of the $^{89}$Zr from the irradiated target.

Figure 2:
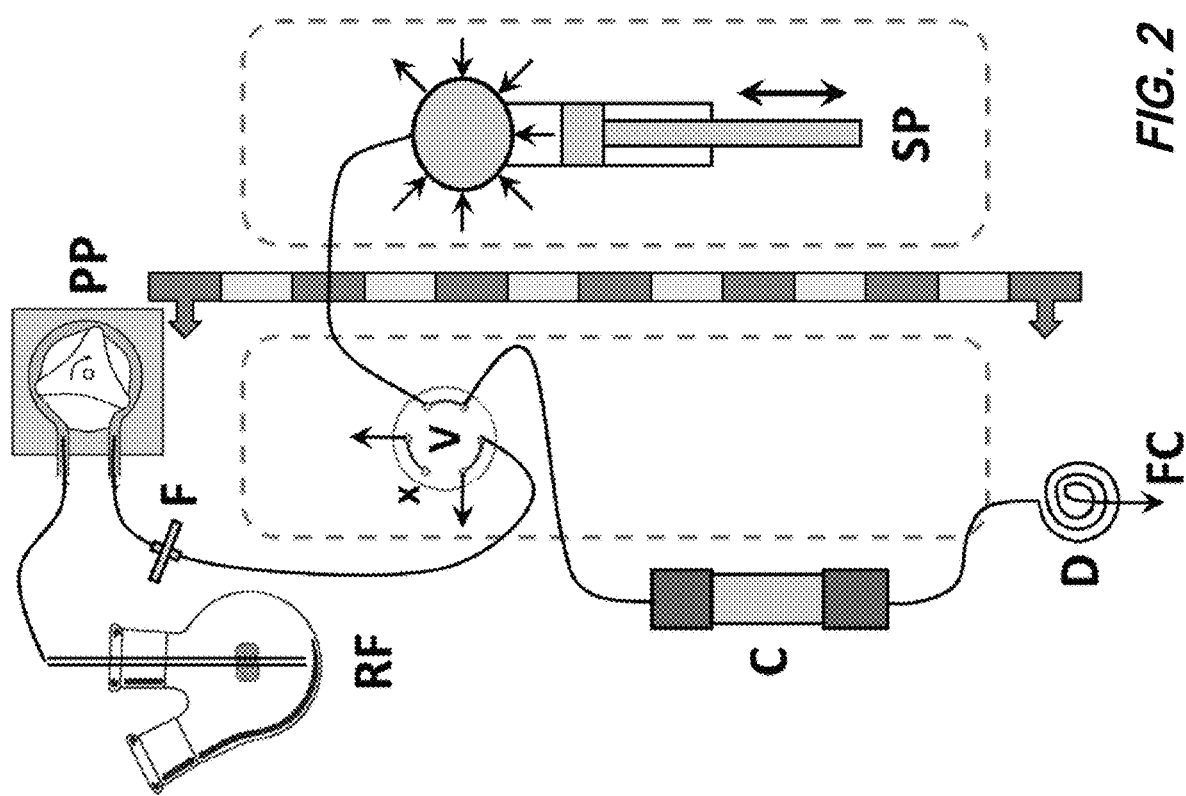

Referring to FIG. 2, delivery of dissolved yttrium target solution to a hydroxamate column, column washing, and $^{89}$Zr elution; in its simplest configuration, the process is accomplished using a syringe pump, a peristaltic pump, and a 2-position valve. The system can incorporate on-line monitoring of column effluents with the use of a NaI(Tl) scintillation detector for example. Beyond the detector, a fraction collector captures column effluents for example.

Figure 3:
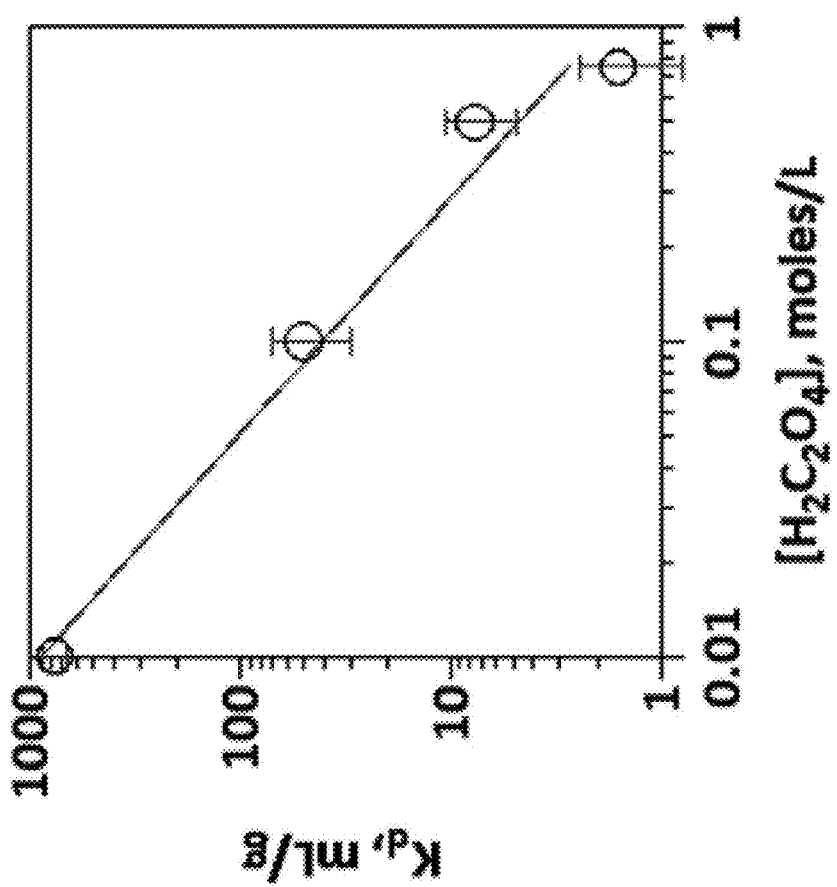
FIG. 3 depicts distribution coefficient ($K_d$) values for $^{88}$Zr tracer on hydroxamate resin as a function of $H_2C_2O_4$ concentration. $^{88}$Zr tracer data is approximated by the curve $y=1.87x^{-1.34}$ ($R^2$=0.972).

The fluidic system has been used to demonstrate the performance of the $^{89}$Zr purification method commonly used in the field. However, the method has been modified to utilize a significantly less concentrated oxalic acid eluent solution (0.8 M), which primarily serves to minimize the quantity of buffering agents required to be added prior to labeling the $^{89}$Zr product. The concentration of oxalic acid used in the field (1 M) can be close to saturation at laboratory temperatures; the solubility limit of $H_2C_2O_4$ in water at 20° C. is 95.2 g·kg$^{-1}$ (1.06 mol·kg$^{-1}$), or a 8.69% (w/w) mass fraction. The methods and systems may reduce the amount of metal contaminants introduced into the product. With reference to FIG. 3, the lower concentration of oxalic acid was shown to be feasible by determining the distribution coefficient ($K_d$) of Zr (as $^{88}$Zr) on hydroxamate resin across a range of oxalic acid concentrations, values which have not previously been reported.

Optima™ grade hydrochloric acid (Fisher Scientific, Waltham, Mass.) was used for Y target dissolution and column washes, and hydrogen peroxide (29-32%, Sigma-Aldrich) was used in the Y target dissolution. TraceSELECT® oxalic acid dihydrate (>99.9999%, Sigma-Aldrich, St. Louis, Mo.) was used for $^{89}$Zr column elutions. All solutions were prepared from deionized water (18.3 MΩ·cm) using a Barnstead Nanopure Diamond water purification system (Dubuque, Iowa). Hydroxamate ligand was bound onto Accell Plus CM weak cation-exchanger (37-55 µm, Waters Corp., Milford, Mass.) by the method of Verel et al. The hydroxamate column was prepared using 100 mg resin packed into a disposable 1 cc SPE column using 2 mm thick polyethylene (PE) frits (Supelco, Bellefonte, Pa.). With an ID of 5.6 mm, the resin bed had a height of ~1.0 cm.

Zirconium-88 ($^{88}$Zr) and yttrium-88 ($^{88}$Y) radiotracers (tracers), with half-lives of 83.4 and 106.6 days, respectively, were purchased through the Department of Energy Office of Science National Isotope Development Center (NIDC). The $^{88}$Zr was periodically purified of in-grown $^{88}$Y using an anion exchange separation method, whereby $^{88}$Zr was loaded onto a ~0.8 cc AG MP-1M column (Bio-Rad Laboratories, Inc., Hercules, Calif.) in concentrated (conc.) HCl ($^{88}$Y is unretained). Then, after a conc. HCl column wash, the $^{88}$Zr was eluted in 6 M HCl. $^{89}$Zr was obtained from the University of Washington (UW) PET radiochemistry center as an irradiated Y foil of 0.25 mm thickness (Alfa Aesar, Ward Hill, Mass.). Following an initial decay period of ~2 h, the $^{89}$Zr target activity was determined by a dose calibrator and corrected to activity at end of bombardment (EOB). Upon delivery to PNNL, this activity was verified using a high purity germanium (HPGe) detector (Ortec, Oak Ridge, Tenn.) calibrated with NIST-traceable standards, with energy and efficiency checks performed daily.

Referring to FIG. 3, distribution coefficients ($K_d$) for each radiotracer ($^{88}$Zr, $^{88}$Y) were determined on synthesized hydroxamate resin across a range of $H_2C_2O_4$ concentrations. Resin contact volumes were typically 5 mL in 2-dram borosilicate glass vials. Sorbent to solution ratios were between ~4 and 20 mg/mL. The resin was initially weighed into tared vials, and the vials were then transferred into a radiological fume hood. Additional vials were included that did not contain resins; these vessels served as controls for determination of the initial activities of $^{88}$Zr and $^{88}$Y for each spiked solution. Reservoirs of $H_2C_2O_4$ solutions were spiked with either $^{88}$Zr or $^{88}$Y and were mixed thoroughly. Next, 5 mL aliquots of the spiked $H_2C_2O_4$ solutions were pipetted into each resin contact and control vessel. Vessels were shaken for ~4 h at ~150 rpm on an orbital shaker. Following the contact period, the vials were removed from the shaker. A second set of clean 2-dram vials were brought into the radiological fume hood. A disposable plastic syringe was used to extract the contacted solution; a 17 mm diameter, 0.45 µm polyethersulfone (PES) syringe filter (Thermo Scientific, Waltham, Mass.) was then attached to the syringe and the resulting filtrate was delivered to the clean vessel. Finally, 2.0 mL of filtrate was transferred to a 12×74 mm test tube for counting on a Wizard 1470 (PerkinElmer, Meriden, Conn.) automatic gamma counter containing a well-type NaI(Tl) scintillation detector. The detector was configured with counting protocols specific to $^{88}$Zr and $^{88}$Y gamma emission regions of interest (corresponding to 393 keV for $^{88}$Zr (97.3% intensity) and 898 keV for $^{88}$Y (93.7% intensity)).

As shown in FIG. 2, the system includes a 48,000 step digital syringe pump (SP) coupled to an 8 position distribution valve (Norgren, Las Vegas, Nev.). The SP was configured with a 10 mL displacement syringe (Flex Fluidics, Las Vegas, Nev.). A 6-port 2-position Cheminert valve (V), driven by a microelectric actuator, was manufactured by Valco, Inc. (Houston, Tex.). The pump and valve were assembled into two separate boxes provided by J-Kem (St. Louis, Mo.), and were operated by a customized version of Kem-Pump software. The pump box was positioned outside the radiological contamination area (RCA) in order to minimize the amount of equipment this zone. A check valve placed in-line with the reagent delivery tubing assured that only flow direction into the RCA was possible. The system was plumbed using 0.5 mm and 0.75 mm ID×1/16" OD Teflon® FEP tubing for reagent transport lines. Lines were connected to the hardware using PEEK 1/4-28 flangeless nuts with Tefzel® ferrules (Upchurch Scientific, Oak Harbor, Wash.) and PEEK 10-32 nuts with PEEK conical ferrules (Valco). The hydroxamate column (C) was inserted into the influent and effluent lines with PEEK luer to 1/4-28 nut couplers. The column effluents were routed through an on-line detector (D) to a fraction collector (FC).

The Y foil was dissolved in a 50 mL 2-neck round-bottom reaction flask (RF) that contained a magnetic stir bar. A 4-channel Sci-Q 400 peristaltic pump (PP) (Watson-Marlow, Wilmington, Mass.) was configured to deliver the Y foil dissolving solution via a tube inserted through the side neck of the RF using pump channel 1 (not shown). Channel 2 of the PP was used to withdraw the dissolved Y foil solution via a polyetherimide (ULTEM™) sipper tube inserted through the central neck. Downstream of the PP, an in-line filter (17 mm diameter, 0.45 µm PES syringe filter (Thermo Scientific) was connected to the delivery line using PEEK luer to 1/4-28 couplers (Upchurch). The dissolved target solution delivery line was then routed to the 6-port 2-position V. In position 1, the V directed the PP flow to a waste line, and in position 2, the PP connected to the column. Inversely, the SP access to the valve's waste and column delivery ports were positions 2 and 1, respectively.

The fluidic system reagent delivery protocol for purifying $^{89}$Zr on a hydroxamate column is summarized in Table 1.

TABLE 1

Automated hydroxamate resin column separation protocol for the load/wash-elute sequence of cyclotron-produced $^{89}$Zr from a dissolved Y metal target.

| Step | Purpose | Reagent | Volume, mL | Flow Rate, mL/min | Valve Position |
|---|---|---|---|---|---|
| 1 | Condition | 2M HCL | 5 | 1.0 | 1 |
| 2 | Load | Y foil in 2M HCl/ 0.1M $H_2O_2$ [a] | 6 | 0.5-0.6 | 2 |
| 3 | Wash 1 | 2M HCl | 10 | | |
| 4[b] | Wash 2 | $H_2O$ | 10 | 1.0 | 1 |
| 5 | Elute | 0.8M $H_2C_2O_4$ | 5[c] | | |

[a] Foil masses ranged from 0.15-0.25 g
[b] At the completion of the step, air was pushed through the column delivery line to purge reagent
[c] Only the first ~1-1.5 mL was collected as the $^{89}$Zr product fraction The column is first conditioned with 2 M HCl by the syringe pump (SP) via the valve (V), which is initially set to position 1. The irradiated Y foil (typically 150-250 mg) is placed in the 2-neck round-bottom flask. The peristaltic pump (PP) is engaged to deliver 6 mL 2 M HCl/0.1 M $H_2O_2$ to the side neck of the flask at a rate of ~6 mL/min. The solution is stirred during dissolution with a magnetic stir bar to minimize frothing and spatter inside the flask. The solution is allowed to cool with stirring for 10-20 min, followed by 5-10 min of settling prior to initiating column load. Next, the dissolved foil solution is delivered to the column at 0.5-0.6 mL/min by the PP through an in-line filter (F) to remove residual solids, and then through the V (toggled to position 2). Once the solution is transferred onto the column, the V is returned to position 1, where the SP is once again connected to the column. The SP sequentially delivers 10 mL of 2 M HCl and 10 mL of $H_2O$ washes to the column at a 1 mL/min flow rate. At the completion of the $H_2O$ wash, and prior to the $^{89}$Zr elution step, the SP pushes air through the column delivery line until all fluid is purged from the column and detector/fraction collector delivery lines. Zirconium-89 can be eluted using 5 mL of 0.8 M $H_2C_2O_4$, for example. The fraction collector is used to separate the elution volumes so only the first ~1-1.5 mL of the elution volume can be used for subsequent evaluation of product labeling performance.

The $^{89}$Zr purification process is 1) fluidically automated, 2) provides near-real time monitoring of column effluents, and 3) uses a significantly lower concentration of $H_2C_2O_4$ (0.8 M) eluent than that reported previously. A schematic of the fluidic device is shown in FIG. 2, while Table 1 describes the computer-controlled $^{89}$Zr separation protocol employed by the device.

Figure 4:
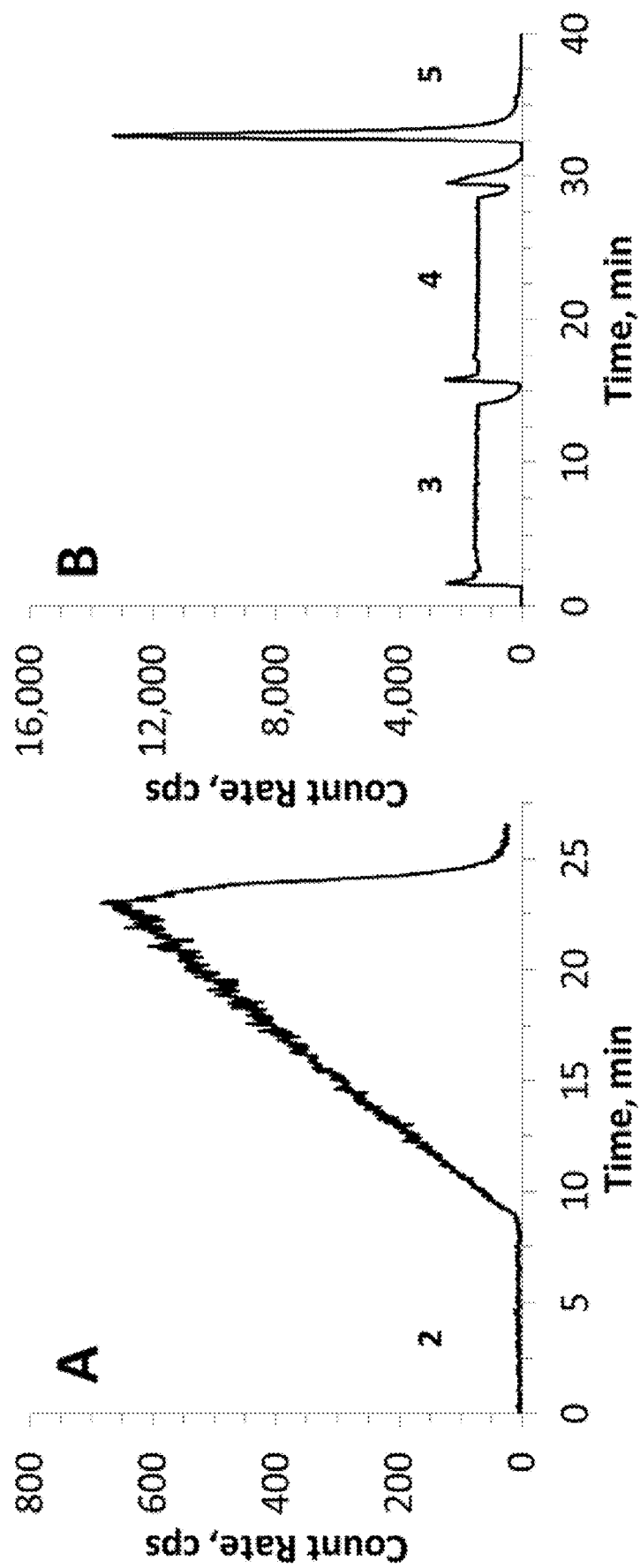
FIG. 4 depicts on-line traces of column effluents during a hydroxamate column separation. (A) Loading $^{89}$Zr from dissolved irradiated Y target onto column. (B) Column washes followed by $^{89}$Zr elution. Except for the $^{89}$Zr elution peak at (5), detected activity is from the sorbed $^{89}$Zr's continuous production of unretained $^{89m}$Y daughter.

On-line detector traces for a hydroxamate resin column separation of $^{89}$Zr from an irradiated Y foil target are shown in FIG. 4. For this run, the irradiated Y foil (165 mg) contained 3.46 mCi $^{89}$Zr (EOB). Note that the NaI(Tl) scintillation detector was raised above the detection loop prior to the start of the run to assure that the $^{89}$Zr elution peak would not saturate the detector. The detector trace for the column load step (via the PP) is shown in FIG. 4A (step 2 in Table 1). The trace shows a continuous increase in detector response over time. As the $^{89}$Zr concentrates on the column, an ever-increasing amount of the short-lived and un-retained $^{89m}$Y daughter is being delivered to the detector. The rapid drop in detector response at ~23 min corresponds to the completion of loading the dissolved target onto the column, as air has been pushed through the column and detector loop.

FIG. 4B shows the on-line detector trace for steps 3-5 in Table 1. During the 2 M HCl (3) and $H_2O$ (4) deliveries, the detector signal rises and plateaus. The signal corresponds to the delivery of unretained $^{89m}$Y that is being continuously generated by the $^{89}$Zr parent that is sorbed on the column. For a given activity of sorbed $^{89}$Zr, the $^{89m}$Y detector response is a function of the effluent flow rate and the internal tube volume between the column and the detector. Dips in the detector signal are caused by the stopping/reloading of the SP between reagent deliveries, as the $^{89m}$Y quickly decays within the detector cell during these disruptions in flow. Activity spikes at each resumption in flow are $^{89m}$Y that has in-grown on the column during the brief pauses of the syringe. Finally, the elution of $^{89}$Zr is shown at the end of the trace (5).

Five Y foils were irradiated and then processed as per the described hydroxamate resin column method. Table 2 provides a summary of the $^{89}$Zr activities (at EOB) and masses for each foil, as well as the chemical separation performance of $^{89}$Zr from the dissolved foils.

TABLE 2

Activity distribution of $^{89}$Zr loaded onto a hydroxamate resin column across five irradiated Y foil targets.

| Foil ID | $^{89}$Zr Activity, mCi [a] | Foil Mass, mg | $^{89}$Zr Distribution from Hydroxamate Column, % [b] | | | |
|---|---|---|---|---|---|---|
| | | | Load | Wash 1 | Wash 2 | Elute [d] |
| 1 | 1.69 | 244 [c] | 1.9 | 0.3 | 0.0 | 97.6 |
| 2 | 0.16 | 252 [c] | 1.2 | 0.1 | 0.0 | 98.6 |
| 3 | 0.66 | 249 [c] | 0.2 | 0.1 | 0.0 | 99.7 |
| 4 | 4.51 | 153 | 0.2 | 0.0 | 0.5 | 99.3 |
| 5 | 3.46 | 165 | 0.0 | 0.0 | 0.0 | 99.9 |
| Average ± 1σ [e] | | | 0.7 ± 0.8 | 0.1 ± 0.1 | 0.1 ± 0.2 | 99.0 ± 0.9 |

[a] At end of bombardment (EOB)
[b] Total activity recovered from the column separation
[c] Foil mass supplemented with unirradiated Y foil
[d] $^{89}$Zr recovery in 5 mL elution volume
[e] Sample standard deviation Irradiated foils 1-3 were originally ~150-180 mg, but the mass was augmented with the addition of unirradiated Y foil to ~250 mg in order to assure the robustness of the method. Foils 4 and 5 received no additional Y foil. For each $^{89}$Zr purification, all column effluents were collected in order to determine the fraction of $^{89}$Zr activity at each step. The total elute fraction contained 99.0±0.9% of the column-loaded activity. However, some $^{89}$Zr activity was lost to the system, either in the form of residues remaining from the foil dissolution (activity remaining in the reaction flask and in-line membrane filter) or as activity trapped in the column. Residual $^{89}$Zr activity was calculated to be 4±1% of the original foil activity. Considering the $^{89}$Zr activity lost to the system, the total $^{89}$Zr yield in the elution fractions was 95±2% of the $^{89}$Zr present in the irradiated Y foil.

The elution profiles for four replicate $^{89}$Zr purification runs are shown in FIG. 5. The vertical scale is normalized to the peak maximum of each elution profile for ease of comparison. Zero volume is set at the point at which the SP begins delivering eluent solution to the column delivery line, which was purged with air prior to this step. The elution peaks began entering the detector after 1.21±0.03 mL was delivered to the system (vertical dashed line). Thereafter, the peak maximum was obtained after 0.33±0.04 mL; 90% and 95% of the elution activity was obtained after 1.02±0.09 mL and 1.71±0.15 mL, respectively. One milliliter fractions collected from the elution profiles in FIG. 5 represent 89±2% of the $^{89}$Zr eluted from the columns. When considering the fraction of $^{89}$Zr lost to the system, the 1 mL elution fraction represents 84±2% of the total $^{89}$Zr present in the irradiated target.

With reference to FIG. 1 again, a different resin can be utilized, for example an ion exchange resin. The resin of this embodiment may be strongly basic anion exchange resin, gel-type or macroporous resin, that may include styrene divinylbenzene polymer or acrylic polymer. Accordingly, methods are provided for purifying $^{89}$Zr that can include: preparing a loading solution comprising $^{89}$Zr and HCl; exposing the loading solution to an anion exchange resin; and eluting the $^{89}$Zr from resin using an HCl solution having a molarity greater than 0.3. In accordance with example implementations, the HCl solution may have a molarity between 0.3 and 9, or between 2 and 6. The HCl solution may have a molarity of at least 0.3. In accordance with additional implementations, the HCl solution may also include fluoride, in ion form, for example NaF.

In accordance with example implementations, three strongly basic anion exchange resins were evaluated. Each had quaternary amine functional groups with different polymer supports. The supports ranged from macroporous and 10% cross-linked styrene-divinylbenzene copolymer to a hydroxylated methacrylic polymer. The resins were evaluated for their ability to load and elute Zr in neat solutions and solutions containing high concentrations of dissolved Y. Additionally, the method had to ensure removal of Fe (a metal that competes for antibody labeling sites for example) from the Zr product. In accordance with example implementations, eluent solutions are provided to remove $^{89}$Zr selectively to Fe(III). Accordingly, after a dissolved irradiated Y foil was loaded and subsequently washed, both $^{89}$Zr and Fe may remain on the resin. Eluting solutions are provided that elute $^{89}$Zr while leaving Fe(III) on the resin.

The $^{89}$Zr purification method involves cyclotron bombarded Y foil dissolution, loading of $^{89}$Zr from the dissolved target onto an anion exchange column, column wash, and $^{89}$Zr elution. This sequence of steps was accomplished with a prototype automated fluidic platform (FIG. 6) configured with an on-line gamma detector and in-line UV-Vis absorbance detector to monitor $^{89}$Zr and Fe(III) column effluents respectively in near-real time.

TraceMetal and Optima grade hydrochloric acid (34-37% HCl, Fisher Scientific) working stock solutions were prepared as-is or as dilutions into deionized water (18.3 MΩ·cm) using a Barnstead E-Pure water purification system (Dubuque, Iowa). Method development work and cyclotron bombarded Y foil processing used TraceMetal and Optima grade acids, respectively. Sodium fluoride (99.99+ %) and hydrogen peroxide (30%) were purchased from Sigma-Aldrich (Milwaukee, Wis.). Several ion exchange resins were evaluated: AG MP-1M (Cl⁻ form, 200-400 mesh) and AG 1-X10 (Cl⁻ form, 100-200 mesh) strongly basic anion exchangers, each on styrene-divinylbenzene co-polymer (Bio-Rad Life Science, Hercules, Calif.), and Toyopearl QAE-550C strongly basic anion exchanger (Cl⁻ form, 50-150 μm) on hydroxylated methacrylic polymer (TOSOH Bioscience, King of Prussia, Pa.).

As depicted in FIG. 6, a fluidic system was configured with a 48,000 step digital syringe pump (SP) with an 8-position distribution valve (Kloehn, Las Vegas, Nev.) and a 10 mL zero-dead-volume syringe (FlexFluidics, Las Vegas, Nev.). Two Cheminert valves coupled to microelectric actuators (Valco Instruments Co, Inc., Houston, Tex.) allowed fluids to be directed into various flow paths. (FIG. 6, left). Valve 1 (V1) was a 6-port 2-position valve and Valve 2 (V2) was a 4-port 2-position valve. The hardware was packaged into separate pump and valve boxes by J-KEM (St. Louis, Mo.), and was controlled by a modified version of Kem-Pump software (J-KEM). All transport and reagent lines were made from 0.5 mm and 0.75 mm i.d. fluorinated ethylene propylene (FEP) tubing (Upchurch Scientific, Oak Harbor, Wash.), respectively. Fittings were made from polyether ether ketone (PEEK), of either ¼-28 (Upchurch) or 10-32 (Valco) thread size. Ferrules were ethylene tetrafluoroethylene (ETFE) or FEP. The column was 4.6×50 mm (0.83 cc internal volume), made by OmegaChrom (Upchurch), with frits from IsoLab, Inc. (Akron, Ohio). The column delivery and exit lines were plumbed into the 4-port 2-position V2 such that flow to the column could be directed to either the forward flow (FF) or reverse flow (RF) direction, depending on valve position.

Two automated fluid delivery protocols were prepared for optimization of $^{88}$Zr tracer separation methods on ion exchange columns. For initial column performance studies, $^{88}$Zr tracer was introduced to the column using a 0.29 mL sample loop configured within a 6-port 2-position valve (V1). A description of the protocol is shown in Table 3, and the system is illustrated in FIG. 6, left.

TABLE 3

Chemical separation protocol for load/wash-elute-strip sequence on columns for determination of optimal eluent for $^{88}$Zr.

| Step | Purpose | Reagent | Volume, mL[a] | V1 Position[b] |
|---|---|---|---|---|
| 1 | Condition | Conc. HCl | 5 | 1 |
| 2 | Load[c] | $^{88}$Zr in Conc. HCl | 5 | 2 |
| 3 | Wash | Conc. HCl | | |
| 4 | Elute | Variable HCl concentrations | 7.5 | 1 |
| 5 | Strip | 3M HCl + 0.1M NaF | 4 | |

[a]Flow rate 0.75 mL/min; all flow in forward direction through column
[b]V2 is in position 1 for duration of run
[c]Delivered via 0.290 mL sample loop through a 6-port 2-position valve The SP was programmed to deliver reagents at 0.75 mL/min. With V1 in position 1, the sample loop (SL) was isolated, and the SP delivered solutions directly to the column to be conditioned with conc. HCl. Next, the $^{88}$Zr was loaded onto the column by toggling V1 to position 2, whereby a 5 mL aliquot of load solution from the SP pushed the $^{88}$Zr-bearing solution to the column and subsequently washed the column. Next, 7.5 mL of $^{88}$Zr eluent solution (varying between 0.1 and 9 M HCl) was delivered to the column, followed by 4 mL of strip solution to ensure all $^{88}$Zr was removed from the column and the tubing.

Once the optimal separation media and $^{88}$Zr tracer eluent solution was selected, a second fluid delivery protocol was prepared, and is summarized in Table 4.

TABLE 4

Chemical separation protocol for the load/wash-elute-strip sequence of $^{88}$Zr and $^{88}$Y from dissolved Y metal (or $^{89}$Zr from a dissolved irradiated foil target) loaded onto an MP-1M column. Flow rate 0.75 mL/min, unless otherwise specified.

| Step | Purpose | Reagent | Volume, mL | V1 Position | Flow Direction[a] |
|---|---|---|---|---|---|
| 1 | Condition | Conc. HCl | 5 | 1 | FF |
| 2 | Load[b] | $^{88}$Zr in Y/Conc. HCl | 20 | 2 | |
| 3 | Vessel Rinse[c] | Conc. HCl | 0.5 (×2) | | |
| 4 | Wash | Conc. HCl | 5 | 1 | |
| 5 | Elute | 6M HCl ± NaF[d] | 5 | | FF/RF[e] |
| 6 | Strip | 3M HCl + 0.1M NaF | 7.5 | | |

[a]V2 configured for FF (forward column flow) or RF (reverse column flow)
[b]Delivery of dissolved Y target solution to column via peristaltic pump (0.5-0.6 mL/min)
[c]2 × 0.5 mL conc. HCl wash of dissolution vessel walls after dissolved target solution was completely aspirated from vessel
[d]Eluents evaluated: 6M HCl, 6M HCl + 0.33 mM NaF, and 6M HCl + 1.0 mM NaF
[e]The eluent solutions in (d) were evaluated under FF and RF directions The hardware was reconfigured to that shown in FIG. 6, right. This protocol enabled the delivery of dissolved Y metal solution to the column via a PP with V1 in position 2, immediately following a 5 mL delivery of conditioning solution via the SP with V1 set to position 1. After delivery of the dissolved Y solution, V1 was reset to position 1 for the remainder of the protocol. This allowed the SP to deliver reagents directly to the column.

Batch contact experiments were performed in order to determine the distribution coefficients ($K_d$) of Zr and Y (as $^{88}$Zr and $^{88}$Y) on two anion exchange resins across a range of HCl concentrations (0.1 to ~12 M). AG MP-1M (MP-1M) and Toyopearl QAE-550C (QAE-550C) were evaluated. A $K_d$ map for Zr on each resin as a function of HCl concentration is shown in FIG. 7. The MP-1M exhibited superior $K_d$ values at high HCl concentrations (~7× higher) when compared to QAE-550C. In no case was $^{88}$Y observed to sorb onto the resins.

The $K_d$ map shows low $K_d$ at HCl concentrations below ~9 M, and steeply rising $K_d$ as the HCl concentration approaches ~12 M. As HCl concentration increases, Zr chloride complexes transition from $ZrCl_4 \rightarrow Zr Cl_5^{-1} \rightarrow ZrCl_6^{-2}$, the latter of which is most strongly retained on the quaternary amine group of the resins.

Both MP-1M and QAE-550C were evaluated for their performance in loading and eluting $^{88}$Zr tracer from a 4.6×50 mm column. The fluidic platform was configured as shown in FIG. 6, left, and the fluid delivery protocol shown in Table 3 was loaded into the instrument controller. Approximately 10 kBq of $^{88}$Zr tracer in conc. HCl was loaded into the 0.29 mL sample loop. The fluid delivery protocol was activated, and it delivered conditioning, sample load/wash, $^{88}$Zr elution, and strip reagents to the column. The on-line detector monitored the activity of the column effluents over time, and the fraction collector, in tandem with the detector, collected each reagent into a separate vial for off-line counting.

FIG. 8 shows a zoomed-in view of the radiochromatograms collected using an MP-1M column, with time zero corresponding to the beginning of the syringe pump delivery of eluent to the $^{88}$Zr tracer-loaded and washed column. The eluent solutions (7.5 mL) were varied between 0.1 and 9 M HCl, with only 1, 6, 7.5, and 9 M HCl eluent radiochromatograms included in the figure. Subsequent to the delivery of the eluent, the syringe pump loaded 4 mL of strip solution (3 M HCl+0.1 M NaF) and delivered it to the column to remove any residual Zr. The concentration of HCl in the eluent solution had a dramatic effect on the elution profile of the $^{88}$Zr tracer, with peaks broadening as the HCl concentration increased. At 9 M HCl, no $^{88}$Zr was removed from the column during the elution cycle. The other observation of note is the incomplete elution of $^{88}$Zr during the elution cycle across all concentrations of HCl. In each case, a discernable fraction of $^{88}$Zr tracer remained uneluted within the 7.5 mL elution window, only to be expeditiously removed from the column during the strip cycle. The fraction of $^{88}$Zr found in the elute and strip solutions for 0.1 to 9.0 M HCl are listed in Table 5.

TABLE 5

Performance of anion exchange resins on the recovery of $^{88}$Zr following the load/wash-elute-strip routine described in Table 3. Values represent the fraction of $^{88}$Zr tracer measured between the elute and strip solution deliveries vs. total loaded activity.

| | 4.6 × 50 mm Column[a,b] | | | |
|---|---|---|---|---|
| | MP-1M | | QAE-550C | |
| [HCl], M | Elute | Strip | Elute | Strip |
| 0.1 | 0.43 | 0.56 | | |
| 0.3 | 0.53 | 0.47 | 0.92 | 0.08 |
| 1.0 | 0.65 | 0.35 | 0.93 ±0.04 | 0.07 ±0.04 |
| 2.0 | 0.72 | 0.28 | 0.97 ±0.01 | 0.03 ±0.01 |
| 3.0 | 0.78 ±0.01 | 0.22 ±0.00 | 0.96 ±0.02 | 0.04 ±0.02 |
| 4.5 | 0.83 | 0.17 | 0.97 ±0.01 | 0.03 ±0.01 |
| 6.0 | 0.86 ±0.04 | 0.14 ±0.05 | 0.97 ±0.01 | 0.03 ±0.01 |
| 7.5 | 0.82 ±0.03 | 0.18 ±0.02 | 0.98 ±0.02[c] | 0.02 ±0.02 |
| 9.0 | <0.01 | 1.00 | 0.97 ±0.02[c] | 0.02 ±0.01 |

[a]$^{88}$Zr activity distribution determined by off-line gamma counting of collected fractions
[b]$^{88}$Zr load/wash fraction not shown (typically <1%), but is included in calculations
[c]Despite high apparent $^{88}$Zr recovery, elution peaks were very broad The activity in the eluent fraction from the MP-1M resin is poor at low concentrations and increases to a maximum at 6 M HCl (0.86±0.04 elute/0.14±0.05 strip), above which it decreases slightly, and ultimately falls to near zero at 9 M HCl.

The incomplete elution of $^{88}$Zr tracer on the macroporous MP-1M prompted the evaluation of the more traditional gel-type anion exchange resin AG 1-X10 (Bio-Rad) under the same conditions. However, the elution profile at 6 M HCl was virtually identical to MP-1M at the same acid strength (0.81 elute/0.13 strip).

The experiments were repeated with the column packed with QAE-550C across a range of HCl concentrations QAE-550C exhibited significantly improved chromatographic performance, with a substantially higher elute fraction across all HCl concentrations tested. $^{88}$Zr tracer elution recoveries were observed between HCl molarities of 0.3 (~92%) to 9 (~97%). Eluent condition ranges can also be between 2 and 6 M HCl (~97%) (Table 5).

Once the optimal eluent solutions were obtained for MP-1M (6 M HCl) and QAE-550C (2 M to 6 M HCl), the automated protocol was repeated with 15.9 kBq $^{88}$Y tracer in conc. HCl loaded into the 0.29 mL sample loop. Yttrium-88 tracer was observed to be thoroughly removed from the column during the $^{88}$Zr during the load/wash step. Using a 6 M HCl elute solution, the MP-1M and QAE-550C $^{88}$Y distributions for the load/wash—elute—strip fractions were 0.999/0.001/0.000 and 0.998/0.002/0.000, respectively.

Despite MP-1M resin's ability to better retain Zr in the presence of high concentrations of Y, its chromatographic performance was poor, with incomplete elution (vide supra). An approach was therefore sought to improve the column's Zr elution performance. Zr produces chlorofluoro complexes in the general form $(ZrCl_iF_j)^{(4-i-j)}$. The presence of low concentrations of HF across a range of HCl concentrations can have a profound effect on the anion exchange behavior of Zr when compared to the behavior of Zr in HCl alone. Specifically, the presence of HF prevents the steep rise in Zr affinity for anion exchange resin at high HCl concentrations. This is likely caused by the formation of chlorofluoro complexes with high negative charges.

An experimental matrix was performed to determine how effective the fluoride ion ($F^-$) was in enhancing the Zr elution performance. Solution combinations of HCl and fluoride ion (as NaF) were prepared with concentrations ranging between 1 and 6 M (1, 2, 3, 4, 6 M) and 0 and 1 mM (0, 0.1, 0.33, 1.0 mM), respectively. Each solution in this matrix was evaluated for its ability to efficiently elute $^{88}$Zr tracer from a pre-loaded column. FIG. 9 shows the results of the column elution performance matrix, with the z-axis representing the fraction of $^{88}$Zr tracer collected within the 7.5 mL elution volume. The poorest elution performance was exhibited at the lower left corner of the matrix (1 M HCl with no NaF), while the optimal elution performance was at the diagonal opposite corner of the matrix: 6 M HCl with NaF ranging between ~0.33 to 1 mM NaF. At 6 M HCl, this optimal NaF concentration range had a pronounced effect on the $^{88}$Zr tracer elution recovery fraction, assuring >99% recovery from the column within the 7.5 mL elution volume, as compared to 86±4% recovery when using 6 M HCl alone (Table 5).

Simulated dissolved irradiated Y targets were prepared using non-irradiated Y metal spiked with $^{88}$Zr or $^{88}$Y tracers following metal dissolution and solution filtration. One-half gram of Y (Alfa Aesar pieces) was utilized in order to robustly verify method performance, as an actual Y target mass would be expected to be significantly lower than this. Two allotments of 0.5 g Y metal were dissolved in 20 mL conc. HCl each using a 50 mL round-bottom flask (with magnetic stirring). After allowing the solution to cool, the solution was filtered (0.45 μm PES, Thermo Scientific) and spiked to ~1 kBq/mL $^{88}$Zr (solution 1) and 6.5 kBq/mL $^{88}$Y (solution 2) tracers, respectively. The fluidic platform was configured as shown in FIG. 6, right, and the fluid delivery protocol shown in Table 4 was loaded into the instrument controller. FIG. 10 shows the resulting detector traces for the dissolved Y metal load and column wash portions of the $^{88}$Zr and $^{88}$Y tracer-spiked runs through the MP-1M column. During the 20 mL load volume, no $^{88}$Zr tracer breakthrough was observed.

The peristaltic pump was operated until the entire sample volume, plus rinses (0.5 mL×2), had been delivered to the column (the rapid drop in $^{88}$Y tracer signal at the end of the load is air pushed through the detection coil). The small $^{88}$Y peak shown in the wash segment (arrow) represents residual $^{88}$Y droplets removed from the fluid delivery lines plus removal of residual sample load solution trapped in the interstitial spaces of the column. The $^{88}$Y tracer, used as an indicator of the dissolved Y metal in the simulated dissolved target solution, shows virtually complete removal of Y after just a couple of milliliters of wash solution. Of 130 kBq $^{88}$Y tracer in 0.5 g dissolved Y metal delivered to the column, <6 Bq were observed in the subsequent Zr elute fraction (signal was below the gamma detector detection limit). This activity is equivalent to <23 μg Y, and represents a Y decontamination factor (DF) of >22,000.

An additional set of experiments was performed in order to evaluate the Zr loading performance of the MP-1M column across a range of Y concentrations and load volumes in conc. HCl. Table 6 summarizes the load conditions and the observed Zr breakthrough levels.

TABLE 6

$^{88}$Zr loading performance on MP-1M column at various load volumes and Y concentrations.

| Y Conc., | Load Vol., | Flow Rate, | $^{88,\,89}$Zr Breakthrough, % | |
|---|---|---|---|---|
| mg/mL | mL | mL/min | Load | Wash |
| 11.9 ± 0.8$^a$ | 20 | 0.5-0.6 | 1.1 ± 0.8 | 0.0 |
| 19.2 | 10 | | 1.0 | 0.1 |
| 25.0$^b$ | 20 | | 0.0 | 0.0 |
| 39.3 | 5 | | 0.3 | 0.1 |

$^a$Performed on irradiated Y targets ($^{89}$Zr, n = 3)
$^b$$^{88}$Zr spike in 0.5 g dissolved Y, as shown in FIG. 10

Despite the Zr $K_d$ dependence on Y concentration (FIG. 11), no significant level of Zr breakthrough was observed during the load steps, nor was it observed in the subsequent column washes for the Y concentrations and load volumes indicated.

Six separation protocol variations, each representing only a change in the eluent solution delivery, were run using the Table 4 protocol. The load solution contained 0.5 g dissolved Y metal and $^{88}$Zr tracer in 20 mL conc. HCl. The elute (reduced to 5 mL) and strip portion of the detector traces for each run are shown in FIG. 12 (top row). The time gap between the arrows represents the time required for the syringe pump to reload itself with the strip solution (between ~6.6 and 8 min). FIG. 12 (bottom row) shows the cumulative recovery of eluted $^{88}$Zr tracer obtained during the 5 mL eluent solution delivery. The dashed traces represent forward flow (FF) of the elute and strip solution deliveries to the column, while the solid lines show the same solutions delivered under reverse flow (RF) conditions.

Set A shows FF and RF elute and strip traces for $^{88}$Zr with an eluent solution of 6 M HCl. By the end of the FF elution volume, only 91.4% of the retained $^{88}$Zr was removed from the column. For the 6 M HCl RF trace, 98.5% of the $^{88}$Zr was recovered, with 97% being removed in 2.9 mL. Set B shows FF and RF traces when the eluent solution was 6 M HCl+0.33 mM NaF. The presence of fluoride ion causes a discernible sharpening of the elution peak for the FF condition, with the RF condition showing only a slightly enhanced elution profile. The FF condition resulted in 98.9% of the retained $^{88}$Zr tracer being removed in 5 mL, with 97% removal within 2.9 mL, while the RF condition yielded 99.4% recovery in 5 mL and 97% removal within 2.4 mL of the eluent solution. Set C shows the same for an eluent delivery of 6 M HCl+1.0 mM NaF. Here, the increased complexing strength of the higher fluoride ion concentration results in almost indistinguishable $^{88}$Zr tracer elution profiles between FF and RF. The 5 mL elution recoveries are 99.5% and 99.3%, respectively, while 97% is recovered in 2.4 mL for both flow direction conditions. Based on these observed elution profiles, it was concluded that a solution of 6 M HCl+0.33 mM NaF provided essentially equivalent elution profiles of Zr from the MP-1M column, regardless of eluent solution flow direction.

The test Y foils (Alfa Aesar, 0.25 mm thickness) were cyclotron irradiated to produce $^{89}$Zr activities ranging between ~0.2 and 1.6 mCi. The foils were dissolved in conc. HCl, and the resulting solutions delivered to the column as described above; the solutions had Y concentrations between ~9 and ~19 mg/mL.

The fluid delivery protocol outlined in Table 4 was implemented to perform the $^{89}$Zr/Y separation. The $^{89}$Zr was eluted with 6 M HCl+0.33 mM NaF prior to delivery of the column strip solution. Table 7 provides a summary of the performance from eight $^{89}$Zr purification runs performed under three conditions: 1) RF elution direction with no $H_2O_2$ added to the dissolving solution; 2) RF direction with $H_2O_2$ added to the dissolving solution; and 3) FF elution direction with $H_2O_2$ added to the dissolving solution. The table lists the column effluent distributions for $^{89}$Zr determined by off-line measurement of all collected fractions.

In order to account for the distribution of all $^{89}$Zr in the irradiated foil (not only $^{89}$Zr delivered to the column), post-run fluidic system washes were performed, and the solutions were counted off-line. These washes included the round bottom flask and the dissolved target delivery line and filter. Additionally, the washed in-line filter and column were sent to the counting lab to determine $^{89}$Zr activity in the trapped solids. The last two columns of Table 7 present 1) the fraction of $^{89}$Zr lost in the fluidic system as droplets and as insoluble particulate matter (the primary source of $^{89}$Zr activity loss), and 2) the $^{89}$Zr column elute fraction compared to the total $^{89}$Zr present in the irradiated foil.

yield in the elute solution had not been observed during simulated dissolved Y target studies with $^{88}$Zr spike, and is perhaps evidence of a persistent non-anionic Zr complex or colloidal solid formed during cyclotron irradiation or during target dissolution (e.g., zirconium oxide or zirconyl species).

The effect of $H_2O_2$ in the HC dissolver solution on $^{89}$Zr recovery was therefore evaluated. Foils 3-5 (RF direction) were processed as above, but the conc. HCl reagent was spiked to 0.1 M $H_2O_2$ immediately prior to target dissolution. Despite the increased masses of these foils (between ~240 and ~370 mg Y), the amount of $^{89}$Zr lost in the load dropped significantly to <1%. Additionally, the amount of $^{89}$Zr in the strip fraction dropped from ~6% to 0.7±0.4%. The $^{89}$Zr elution fraction recovery now reached 98.9±0.6% of column-delivered effluents, and 95±3% of the overall foil activity. Foils 6-8, performed with $H_2O_2$ in the dissolver solution and the preferred FF column elute direction, performed equally as well, with 97±1% of the column delivered activity, and 96±2% of the overall foil activity, found in the $^{89}$Zr elute fraction.

The $^{89}$Zr product fractions from Foils 6-8 were analyzed for Y, Fe, and Zr by inductively coupled plasma-mass spectrometry. It was determined that the three product fractions contained 0.74±0.38 μg Y from Y target masses that averaged 0.23±0.02 g. This represents a Y decontamination factor of ~3×10$^5$. Iron in the $^{89}$Zr product fractions was below the detection limit of the ICP-MS. Therefore, the mass of Fe present could only be reported as <0.16 μg. Based on the certificates of analysis (COA) for the Y metal

TABLE 7

Results from the optimized MP-1M column separation of $^{89}$Zr from cyclotron irradiated foils. Results shown with and without $H_2O_2$ treatment during Y target dissolution. Flow direction of $^{89}$Zr elute and strip are indicated.

| | $^{89}$Zr Activity, mCi [a] | [Y], mg/mL | Flow Dir. | $H_2O_2$ Added | $^{89}$Zr Distribution on Column, % [c] | | | | Fraction of Total Produced $^{89}$Zr, % | |
|---|---|---|---|---|---|---|---|---|---|---|
| Foil ID | | | | | Load | Wash | Elute | Strip | Insoluble Residues [d] | Elute Fraction [e] |
| 1 | 0.23 | 8.7 | RF | No | 8.1 | 0.3 | 85.8 | 5.8 | 10.2 | 77.0 |
| 2 | 0.53 | 8.8 | | | 10.2 | 0.5 | 83.1 | 6.1 | 9.2 | 75.5 |
| | | | | Average | 9.2 | 0.4 | 84.5 | 5.9 | 9.7 | 76.2 |
| | | | | (± difference) | (2.1) | (0.2) | (2.7) | (0.3) | (1.0) | (1.6) |
| 3 | 0.79 | 18.6 | RF | Yes [b] | 0.4 | 0.0 | 98.4 | 1.2 | 2.1 | 96.4 |
| 4 | 0.18 | 12.1 | | | 0.1 | 0.0 | 99.6 | 0.3 | 7.9 | 91.7 |
| 5 | 0.97 | 13.1 | | | 0.4 | 0.1 | 98.8 | 0.7 | 1.6 | 97.3 |
| | | | | Average | 0.3 | 0.0 | 98.9 | 0.7 | 3.9 | 95.1 |
| | | | | (± 1σ) | (0.2) | (0.0) | (0.6) | (0.4) | (3.5) | (3.0) |
| 6 | 0.19 | 11.6 | FF | Yes [b] | 1.7 | 0.0 | 96.8 | 1.5 | 1.5 | 98.0 |
| 7 | 0.17 | 11.3 | | | 1.5 | 0.0 | 96.4 | 2.1 | 2.3 | 94.2 |
| 8 | 1.56 | 12.8 | | | 0.2 | 0.0 | 98.6 | 1.3 | 2.3 | 96.3 |
| | | | | Average | 1.1 | 0.0 | 97.3 | 1.6 | 2.0 | 96.2 |
| | | | | (± 1σ) | (0.8) | (0.0) | (1.1) | (0.4) | (0.4) | (1.9) |

[a] Activity determined at EOB
[b] 0.1 M $H_2O_2$ added to conc. HCl immediately prior to target dissolution
[c] Activity fraction for all $^{89}$Zr-bearing solutions delivered to the column
[d] Combined activity of $^{89}$Zr trapped in insoluble residues, remaining in dissolution vessel, trapped in in-line filter and column, etc.
[e] Fraction of $^{89}$Zr in elute fraction, considering all activity in irradiated foil The conc. HCl used to dissolve the first irradiated targets did not contain $H_2O_2$ (foils 1 and 2, RF direction). These were small targets, each ~200 mg. Surprisingly, a significant fraction (8-10%) of $^{89}$Zr was lost to the column during the sample load, and ~6% was recovered in the strip fraction. Approximately 10% of the $^{89}$Zr activity was found as insoluble residue. Combined, this resulted in a ~76% $^{89}$Zr eluent recovery from the overall foil activity. The poor $^{89}$Zr foils used in this study, the irradiated foils would be expected to contain 66±38 μg Fe; therefore, a conservative Fe decontamination factor of >410 is reported. However, given the excellent separation of Zr from Fe using this method (FIG. 13), the Fe decontamination factor is likely much higher than this. The COA did not provide a value for elemental Zr in the foil, but the ICP-MS results of the analyzed $^{89}$Zr product fractions indicated that elemental Zr is present in the foil at 0.4±0.1 µg/g, after correction for the 96±2% recovery in the product fraction. Because the concentration of natural Zr in the chosen Y foil will have a pronounced effect on the quality of $^{89}$Zr labeling onto proteins for example, it is imperative that each Y foil source be analyzed. Some Y foils screened over the course of this study contained Zr levels as high as 240 µg/g; Zr concentrations at these levels would not provide good $^{89}$Zr labeling performance, regardless of the non-Zr elemental purity.

Referring next to FIG. 14 an example depiction of a dual resin system 120 that includes a first resin column 122 having a first resin 124 and a second resin column 126 having a second resin 128. In accordance with example implementations the volume of resin 128 can be a fraction of the volume of resin 124. For example, the first resin is at least twice the volume of the second resin. Further, the solution used to elute metals of importance from column 122 can be a loading solution for column 126, making these solutions, eluting and loading, the same in accordance with example implementations.

In accordance with additional implementations and with reference to FIG. 15, system 130 can include the columns and resins of FIG. 14, however valving/pumping configurations can be included in the form of valving/pumping system 132 and 134 respectively. These systems can be operatively coupled to reservoirs that may receive or provide solutions as dictated by the configuration to allow for system 130 to be operated automatically.

Accordingly, methods for purifying $^{89}$Zr are provided with the methods including loading a first resin with a first loading solution. This first loading solution can include dissolved Y foil that includes $^{89}$Zr, for example. The method can then include washing the first resin and then eluting the $^{89}$Zr from the first resin using a first eluting solution. In the case where the first resin is an ion-exchange resin, the elution can be performed with an HCl solution or an HCl and fluoride solution. The method can then include loading the second resin with a second loading solution comprising $^{89}$Zr. In some embodiments, the loading solution for the second resin can be $^{89}$Zr in HCl solution. In some embodiments, the loading solution for the second resin can be $^{89}$Zr in HCl obtained from the eluting solution from the first resin. The $^{89}$Zr on the second resin can be eluted with a second eluting solution such as oxalic acid. In accordance with example implementations, the first resin can be an ion exchange resin and the second resin is a hydroxamate resin or HDEHP resin.

In accordance with example implementations, TraceMetal and Optima grade hydrochloric acid (34-37% HCl, Fisher Scientific) working stock solutions were prepared as-is or as dilutions into deionized water (18.3 MΩ·cm) using a Barnstead E-Pure water purification system (Dubuque, Iowa). Method development work and irradiated Y foil processing utilized TraceMetal and Optima grade acids, respectively. Sodium fluoride (99.99+ %), hydrogen peroxide (30%), and TraceSELECT® oxalic acid dihydrate (>99.9999%) were purchased from Sigma-Aldrich (St. Louis, Mo.). AG MP-1M strongly basic anion exchange resin (Cl$^-$ form, 200-400 mesh), with quaternary amine functional groups on a macroporous styrene divinylbenzene co-polymer (Bio-Rad Life Sciences, Hercules, Calif.) was used for the primary column. Hydroxamate ligand was synthesized onto Accell Plus CM weak cation-exchanger (37-55 µm, Waters Corp., Milford, Mass.) and used for the secondary column. The MP-1M column had internal dimensions of 4.6×50 mm (0.83 cc internal volume) (OmegaChrom column, Upchurch Scientific, Oak Harbor, Wash.), and used frits from IsoLab, Inc. (Akron, Ohio). The hydroxamate column was constructed from a 2 cm long, ~27 µL internal volume, internally tapered mini-column with PTFE frits (GlobalFIA, Fox Island, Wash.).

Two fluidic system configurations were utilized for this work. Initially, a simple fluidic system was assembled to evaluate the performance of a second resin, in this case a single hydroxamate microcolumn, as shown in FIG. 16 (Left). The system included a 48,000 step digital syringe pump (SP) coupled to an 8 position distribution valve (Norgren, Las Vegas, Nev.). The SP was configured with a 2.5 mL displacement syringe (Flex Fluidics, Las Vegas, Nev.). A 6-port 2-position Cheminert valve (V1), driven by a microelectric actuator, was manufactured by Valco, Inc. (Houston, Tex.). The SP and V1 were assembled into separate boxes, and were remotely by computer. The pump box was positioned outside the radiological zone to minimize the amount of hardware therein. A back-flow preventer was installed between the SP and V1 to ensure no radiological solution could backflow out of the radiological zone. A sample loop (SL) of 0.032 mL inner volume was plumbed within V1 as shown. With V1 in position 1, the loop could be filled with a radiotracer spiked solution using a hand-held sample injection syringe (SS), while the SP could deliver reagents directly to the column (C). With V1 in position 2, the SP could drive the contents of the SL to the column. All column effluents were routed through an on-line detector (D), and then to a fraction collector (FC). In accordance with example implementations, the internal volume of the microcolumn housing the hydroxamate was about ~27 microliters; while the primary AnIX column was about 0.83 mL.

The second system was configured for an automated tandem column purification of $^{89}$Zr from irradiated Y foils. It was comprised of two digital syringe pumps (SP1 & SP2), each with 8-position distribution valves. The SP1 and SP2 syringe displacement volumes were 10 mL and 2.5 mL (Flex Fluidics), respectively. A 6-port 2-position valve (V1) and two 4-port 2-position valves (V2 &V3) were Valco Cheminert valves with microelectric actuators. The pumps and valves were assembled into separate. Once again, back-flow preventers were installed in the SP1 and SP2 reagent delivery lines where they crossed the radiological boundary. In lieu of a SL in V1, the second system incorporated the ability to push a dissolved irradiated target solution from a 50 mL round-bottom flask via a peristaltic pump (PP) to the primary column when V1 was in position 2; SP1 could deliver reagent to the C1 when V1 was in position 1. The target dissolution chamber and dissolved target delivery system have been described herein.

Two automated fluid delivery protocols were prepared in order evaluate the load/wash-elute performance of $^{88}$Zr tracer using column-based separations. The first protocol was designed to evaluate the performance of a hydroxamate microcolumn in isolation from the primary anion exchange column. The steps of the automated protocol are presented in Table 8.

TABLE 8

Automated chemical separation protocol for load/wash-elute sequence on hydroxamate microcolumn for determination of column load/elute properties of $^{88}$Zr and $^{88}$Y.

| Step | Purpose | Reagent | Volume, mL$^a$ | V1 Position |
|---|---|---|---|---|
| 1 | Condition | 6M HCl + NaF | 2 | 1 |
| 2 | Load$^b$ | $^{88}$Zr in 6M HCl ± NaF$^c$ | 2.5 | 2 |

TABLE 8-continued

Automated chemical separation protocol for load/wash-elute sequence on hydroxamate microcolumn for determination of column load/elute properties of $^{88}$Zr and $^{88}$Y.

| Step | Purpose | Reagent | Volume, mL[a] | V1 Position |
|---|---|---|---|---|
| 3 | Wash | 6M HCl ± NaF[c] | | |
| 4 | Elute | 0.8M $H_2C_2O_4$ | 2.5 | 1 |

[a]Flow rate is 0.2 mL/min; all flow is in forward direction through column
[b]Sample delivered in a 0.032 mL sample loop via a 6-port 2-position valve
[c][NaF] was varied between 0 and 10 mM Solutions were aspirated into the 2.5 mL syringe and delivered at 0.2 mL/min. With V1 in position 1, the SP could deliver the conditioning solution to the column, while $^{88}$Zr or $^{88}$Y tracer spiked samples remained isolated in the loop. The sample was loaded onto the column, along with 2.5 mL wash solution, after toggling V1 to position 2. Finally, 2.5 mL of $^{88}$Zr tracer eluent solution (0.8 M $H_2C_2O_4$) was delivered to the column after V1 had returned to position 1.

Once ideal load/wash-elute conditions were obtained for the hydroxamate microcolumn, a tandem column purification method for $^{89}$Zr from dissolved Y foil was developed. The separation protocol is presented in Table 9, and the fluidic system shown in FIG. 16 (right).

As herein described, a primary column (MP-1M) eluent solution of 6 M HCl+0.33 mM NaF could be utilized as a transfer agent to a secondary microcolumn packed with hydroxamate resin. Additionally, it demonstrated how a solution of 0.8 M $H_2C_2O_4$ could be utilized to efficiently elute Zr from the hydroxamate microcolumn in a volume (~0.29 mL) that is significantly less than that specified for the traditional method (typically reported as ~1 mL or greater). The next step was to develop a fully automated tandem column Zr separation that would combine the optimized method for an MP-1M column with the optimized hydroxamate microcolumn method as primary and secondary purification stages, respectively.

The hydroxamate column can be traditionally conditioned in 2 M HCl, after which the dissolved irradiated Y target (in ~2 M HCl±$H_2O_2$) is loaded to adsorb the $^{89}$Zr. The column is subsequently washed with 2 M HCl to remove residual Y ions, and is then washed with $H_2O$ to remove residual HCl. The $^{89}$Zr is traditionally eluted with 1 M $H_2C_2O_4$, and the first 1 mL eluent fraction is typically collected for subsequent radiolabeling.

Given the familiarity and reliability of this separation method, it was replicated to the extent possible in the latter steps of the MP-1M→hydroxamate resin tandem column separation scheme. Table 9 summarizes the tandem column

TABLE 9

Automated MP-1M → hydroxamate resin tandem column separation protocol for the purification of cyclotron-produced $^{89}$Zr from dissolved Y metal targets.

| | | Column[a] | | Volume, | Flow Rate, | Valve Position | | |
|---|---|---|---|---|---|---|---|---|
| Step | Purpose | (Pump) | Reagent | mL | mL/min | V1 | V2 | V3 |
| 1 | Condition | C1 (SP1) | Conc. HCl | 5 | 1.5 | 1 | 1 | 1 |
| | | C2 (SP2) | 2 M HCl | 2.5 | 0.4 | 1 | 1 | 1 |
| 2 | Load | C1 (PP) | Y foil in Conc. HCl[b] | 20 | 0.5-0.6 | 2 | 1 | 1 |
| 3 c | Wash 1 | C1 (SP1) | Conc. HCl | 5 | 1.5 | 1 | 1 | 1 |
| 4 | Col. Transfer | C1 → C2 (SP1) | 6 M HCl + 0.33 mM NaF | 5 | 0.2 | 1 | 2 | 1 |
| 5 [c] | Wash 2 | C2 (SP2) | 2 M HCl | 2.5 | 0.4 | 1 | 1 | 1 |
| 6 [c] | Wash 3 | | $H_2O$ | 2.5 | | 1 | 1 | 1 |
| 7 [c] | Elute | | 0.8 M $H_2C_2O_4$ | 2.5[d] | 0.2 | 1 | 1 | 2 | aFor C1/C2 and SP1/SP2/PP designations, see FIG 16 (Right)
[b] Target dissolver solution consisted of conc. HCl + 0.1 M $H_2O_2$
[c] At the completion of the step, air was pushed through the column delivery line to purge reagent
[d]Only first ~0.25-0.30 mL was collected as the $^{89}$Zr product fraction Initially, the primary (C1) and secondary (C2) columns were conditioned with conc. HCl and 2 M HCl using SP1 and SP2, respectively. Next, the primary column was loaded with the $^{89}$Zr from the dissolved Y metal target using the PP. Following sample load, the primary column was washed with additional conc. HCl using SP1 to remove all traces of dissolved Y. The $^{89}$Zr on the primary column was then transferred to the secondary column by toggling V2 to position 2 and delivering 5 mL of 6 M HCl+0.33 mM NaF with SP1 to both columns. With all $^{89}$Zr activity now on the secondary column, SP2 commenced to deliver 2 M HCl and $H_2O$ wash solutions, respectively. Finally, the $^{89}$Zr was eluted from the secondary column, using 0.8 M $H_2C_2O_4$, to $^{89}$Zr product collection vessels (CV) with V3 positioned to position 2. While in route from the microcolumn, the $^{89}$Zr elution profile was monitored by the in-line gamma detector.

separation protocol that was employed using the fluidic system shown in FIG. 16 (Right). Steps 1-4 largely cover the primary column (C1) separation of $^{89}$Zr from the dissolved Y target, as described previously. Step 4 (column transfer) coincides with the initiation of the secondary column separation, as the $^{89}$Zr eluent from the primary MP-1M column is synonymous with the load of the $^{89}$Zr onto the secondary microcolumn. The column transfer step is made possible via the fluidic coupling of the primary column effluent with the secondary column influent by setting V2 to position 2 and delivering the transfer solution with SP1.

With reference to Table 10 and FIG. 17, the hydroxamate resin microcolumn (C2), which was already conditioned using 2 M HCl during step 1, is capable of receiving the $^{89}$Zr in 6 M HCl ($K_d$~11,600 mL/g, Table 10) or in 6 M HCl+0.33 mM NaF solution ($K_d$~9000 mL/g, FIG. 17). Following the column transfer step, the C2 is washed with 2 M HCl (using SP2) to remove any trace contaminants that may have bled from the primary column. The column is then washed with $H_2O$ to remove HCl from the column and its connecting lines. After purging the column influent/effluent lines with air, the $^{89}Zr$ is eluted from the column with 6 M HCl+0.22 mM NaF solution, through an on-line detector, and finally to $^{89}Zr$ product collection vials using 2.5 mL of 0.8 M $H_2C_2O_4$. This is accomplished by toggling V3 to position 2. The first 0.25-0.3 mL of column effluent was collected as the $^{89}Zr$ product fraction; the remaining elution volume was collected in a separate vessel in order to determine total $^{89}Zr$ elution recovery.

TABLE 10

Distribution coefficient ($K_d$) values determined using $^{88}Zr$ tracer on hydroxamate resin across a range of HCl concentrations.

| [HCl], M | $K_d$, mL/g | n |
|---|---|---|
| 1 | 5800 | 1 |
| 2 | 12,300 | 1 |
| 3 | 11,300 | 1 |
| 6 | 11,600 ±2200 | 4 |
| 7.5 | 11,000 ±100 | 2 |
| 9 | 14,700 | 1 |
| 12 | 3000 | 1 |

On-line detector traces for a tandem column separation of $^{89}Zr$ from an irradiated Y foil target are shown in FIG. 18. Numbers on the detector traces correspond to the steps listed in Table 9. For this run, the column effluent lines were reconfigured so that the entire separation process could be monitored by the on-line detector. Because of the vastly higher activity levels in the irradiated foil vs. the $^{88}Y$ and $^{88}Zr$ tracer studies, the detector was raised ~15 cm above the detection flow cell. The detector trace for the dissolved target load on the primary column is shown in FIG. 18A. The irradiated Y foil contained 2.11 mCi $^{89}Zr$ (EOB). The foil was dissolved in 20 mL conc. HCl+0.1 M $H_2O_2$ and was loaded onto the primary column at a flow rate of ~0.6 mL/min. FIG. 18B shows the on-line detector trace for steps 3-7 in Table 9. The positive detector responses across steps 2-6 are not due to $^{89}Zr$. Rather, these signals are due to the unretained and short-lived (15.66) $^{89m}Y$ that is generated by the $^{89}Zr$ parent. An explanation of $^{89m}Y$ behavior during the $^{89}Zr$ purification process on a 100 mg hydroxamate column has been given previously. Finally, the $^{89}Zr$ elution is shown at the end of the trace (7).

A total of seven cyclotron bombarded yttrium metal foils were cyclotron irradiated and processed as per the described tandem column method. Table 11 provides a summary of the $^{89}Zr$ foil activities (at EOB) and masses, as well as the chemical separation performance of $^{89}Zr$ from the dissolved foils.

TABLE 11

$^{89}Zr$ separation performance for MP-1M → Hydroxamate tandem column method across seven irradiated Y foil targets.

| Foil ID | $^{89}Zr$ Activity, mCi | Foil Mass, mg | $^{89}Zr$ Distribution from Tandem Columns, % [a] | | | | | |
|---|---|---|---|---|---|---|---|---|
| | | | C1 Load | C1 Wash | C1 → C2 Transfer | C2 Wash [b] | C2 Elute [c] | Strip [d] |
| 1 | 2.11 | 251 | 0.2 | 0.0 | 0.0 | 0.0 | 97.5 | 2.3 |
| 2 | 4.33 | 240 | 0.4 | 0.0 | 3.7 | 0.6 | 94.5 | 0.7 |
| 3 | 1.43 | 252 | 0.9 | 0.0 | 1.6 | 0.3 | 96.2 | 1.0 |
| 4 | 1.80 | 224 | 0.1 | 0.0 | 0.1 | 0.1 | 98.3 | 1.4 |
| 5 | 0.72 | 250 | 0.3 | 0.0 | 0.1 | 0.0 | 96.8 | 2.0 |
| 6 | 5.61 | 175 | 0.1 | 0.0 | 0.8 | 0.2 | 98.3 | 0.6 |
| 7 | 5.48 | 179 | 0.2 | 0.0 | 1.4 | 1.2 | 96.0 | 1.2 |
| Average ±1σ | | 224 ± 34 | 0.3 ± 0.3 | 0.0 ± 0.0 | 1.1 ± 1.3 | 0.3 ± 0.4 | 96.8 ± 1.4 | 1.3 ± 0.6 |

[a] Total activity recovered from the column separation

[b] Cumulative activity fraction across 2 M HCl and H2O washes

[c] $^{89}Zr$ recovery from entire 2.5 mL elution volume

[d] Strip solution was 3 M HCl + 0.1 M NaF, which assured complete removal of any $^{89}Zr$ remaining on the column Irradiated foils 1-5 were originally between 78 and 180 mg, but the mass was augmented with the addition of non-irradiated Y foil to ~250 mg in order to assure that the hydroxamate microcolumn performance was robust. Foils 6 and 7 received no additional Y foil. Irradiated Y foils were dissolved with a solution of 20 mL conc. HCl+0.1 M $H_2O_2$. For each of the seven $^{89}$Zr purifications, all column effluents were collected in order to determine the fraction of $^{89}$Zr activity at each step. The hydroxamate microcolumn elute fraction contained 96.8±1.4% of the column-recovered activity. However, some $^{89}$Zr activity was lost to the system, either in the form of residues remaining from the foil dissolution (activity remaining in the reaction flask and in-line membrane filter) or as activity trapped in the two columns. Residual $^{89}$Zr activity was calculated to be 1.9±0.4% of the original foil activity. Considering the $^{89}$Zr activity lost to the system, the total $^{89}$Zr yield in the elution fractions was 95.1±1.3% of the total $^{89}$Zr foil activity.

The elution profiles for $^{89}$Zr from the hydroxamate microcolumn are shown for four replicate runs in FIG. 19. The vertical scale is normalized to the peak maximum of each elution profile. Zero volume is set at the point at which the syringe pump begins delivering eluent solution to the reagent delivery line, which is purged with air prior to this step. The elution peak begins entering the detector after 0.536±0.002 mL has been delivered to the system. The peak maximum is obtained after 0.045±0.005 mL; full peak width at half the peak maximum (FWHM) is 0.12±0.03 mL. Ninety percent and 95% of the elution activity is obtained after 0.29±0.06 mL and 0.50±0.10 mL, respectively. Given the above result of 95.1±1.3% of the $^{89}$Zr found in the total 2.5 mL elution volume with respect to the activity in the irradiated foil, a 0.29±0.06 mL product volume (90% of elution peak) would be expected to yield 86±5% of the activity in the foil. Accordingly, $^{89}$Zr compositions are provided having 86±5% of the activity in the irradiated foil.

In order to establish a purity measurement specific for $^{89}$Zr compositions analysis methods were developed. For example, Deferoxamine is a bacterial siderophore that is the principal conjugate used to radiolabel proteins with $^{89}$Zr in immunoPET applications. However, metal contaminants that may persist in the $^{89}$Zr product fraction following hydroxamate column purification from the irradiated foil may decrease $^{89}$Zr binding yields. These metals include Zr, Fe, Ga, Al, etc. In general, the concentration of these potentially interfering metals in the $^{89}$Zr product fractions are dependent on the impurity levels in the Y target metal, the target mass required for irradiation, and the decontamination factors made possible by the chemical purification method employed. Commercially available deferoxamine mesylate (Dfo-m) was used to assess the quality of the $^{89}$Zr product fractions that were collected from the automated hydroxamate resin column purification method described above.

The following reagents were used for $^{89}$Zr labeling of deferoxamine mesylate (Dfo-m): Deferoxamine mesylate salt was obtained from Santa Cruz Biochemicals (≥98%) and Sigma-Aldrich (99.0%). Dimethyl sulfoxide (DMSO, ACS Reagent ≥99.9%), sodium carbonate (TraceSELECT®), sodium chloride (TraceSELECT®), and 4-(2-Hydroxyethyl)piperazine-1-ethanesulfonic acid (HEPES, ≥99.5%) were supplied by Sigma-Aldrich. 2,5-Dihydroxybenzoic acid (gentisic acid, 99%) was supplied by Acros Organics (New Jersey).

Parameters that were evaluated in this assessment included bindable metal concentration ($[M_B]$) and effective specific activity (ESA). Two $^{89}$Zr/Dfo-m binding solution matrices were used to determine these parameters for $^{89}$Zr product fractions from each of three irradiated Y targets purified by the method described above.

TABLE 12

Chemical compositions used in $^{89}$Zr/Dfo-m binding studies.

| Method | Preparation Tube | Reagent | Volume, μL |
|---|---|---|---|
| 1 | 1 | $^{89}$Zr Product Mix[a] | 40-80 |
|  |  | 0.2-24 μM Dfo-m | 3-60 |
|  |  | Total Vol. | 43-140 |
| 2 | 1 | $^{89}$Zr Product[b] | 10 |
|  |  | Buffer mix 1[c] | 19.5 |
|  | 2 | Buffer mix 2[d] | 0.6-70.5 |
|  |  | Buffer mix 3[e] | 0-69.9 |
|  |  | Total Vol. | 100 |

[a] $^{89}$Zr product in 0.8M $H_2C_2O_4$ diluted with 0.2M $Na_2CO_3$ and $H_2O$
[b] $^{89}$Zr product in 0.8M $H_2C_2O_4$
[c] Buffer mix 1 = 0.37M $Na_2CO_3$; 0.36M HEPES
[d] Buffer mix 2 = 0.15M NaCl; 0.25M HEPES; 0.014M gentisic acid; 8.37 μM Dfo-m; 0.77M DMSO
[e] Buffer mix 3 = 0.15M NaCl; 0.25M HEPES; 0.014M gentisic acid Method 1 employed a simple solution preparation that consisted of only $H_2C_2O_4$, $Na_2CO_3$ and $H_2O$ in an attempt to minimize the addition of competitive metals from impurities in reagents (Table 12); Method 2 used a more complex solution mixture that incorporated saline, buffers ($Na_2CO_3$ and HEPES), and gentisic acid (an anti-oxidant), similar to that reported by Verel et al. Both methods resulted in solutions with a pH of ~7.

Following solution mixing and incubation, the $^{89}$Zr binding fraction was determined with the use of an aminopropyl-based anion exchange cartridge. Zirconium-89 oxalate (likely $^{89}$Zr $(C_2O_4)_4^{-4}$) that was successfully transchelated to Dfo-m ($^{89}$Zr/Dfo-m) was not retained on the resin, while non-transchelated $^{89}$Zr$(C_2O_4)_4^{-4}$ was retained. The $^{89}$Zr/Dfo-m binding fraction was plotted as a function of added Dfo-m concentration, and a sigmoidal curve was fitted (FIG. 20). The curve was then used to identify the Dfo-m concentration that corresponded to 50% $^{89}$Zr binding, and the bindable metal ($M_B$) content and effective specific activity (ESA) were subsequently calculated. In order to more easily compare the $M_B$ content between Y foil targets of different masses (and, hence, different levels of metal impurities introduced into the purification process), the $M_B$ concentration ($[M_B]$) was calculated (where $[M_B]=M_B/g\ Y$).

Table 13 provides details of the Dfo-m transchelation experiments for Methods 1 and 2 using $^{89}$Zr product fractions obtained from Foils 3-5 using the hydroxamate resin column-based $^{89}$Zr purification method.

TABLE 13

Labeling performance of $^{89}$Zr products evaluated by DFOM transchelation using two solution preparation methods.

| Foil ID | Method | $^{89}$Zr product vol. fraction, $v/v_{tot}$, % | Final [H$_2$C$_2$O$_4$] mM | [M$_B$] nmole·g$^{-1}$ | ESA Ci·mmole$^{-1}$ $^a$ | ESA TBq·mmole$^{-1}$ $^a$ |
|---|---|---|---|---|---|---|
| 3 | 1 | 3.7 | 29 $^b$ | 75.9 | 1200 | 44.24 |
|   | 2 | 10 | 80 | 36.5 | 2494 | 92.26 |
| 4 | 1 | 1.3 | 11 $^c$ | 110 | 1358 | 50.23 |
|   |   | 3.5 | 83 $^b$ | 130 | 1144 | 42.31 |
|   | 2 | 10 | 80 | 41.1 | 3625 | 134.1 |
| 5 | 1 | 1.3 | 11 $^c$ | 95.0 | 1447 | 53.55 |
|   |   | 1.9 | 45 $^b$ | 141 $^d$ | 973 | 35.98 |
|   |   | 3.5 | 83 b | 140 | 982 | 36.32 |
|   | 2 | 10 | 80 | 508 $^d$ | 2705 | 100.1 |
|   |   | Method 1 mean (±1s) $^e$ |   | 115 ± 27 | 1180 ± 190 | 44 ± 7 |
|   |   | Method 2 mean (±1s) $^e$ |   | 43 ± 7 | 2940 ± 600 | 109 ± 22 |

$^a$ Based on 22.7 mCi (841 MBq) $^{89}$Zr produced in a 1 h target irradiation.
$^b$ Na$_2$CO$_3$ and H$_2$C$_2$O$_4$ concentrations were equimolar.
$^c$ Na$_2$CO$_3$ molarity twice the H$_2$C$_2$O$_4$ molarity.
$^d$ 89Zr/DFOM binding fraction plots shown in FIG. 20.
$^e$ Where "s" is the sample standard deviation.

Method 1 employed a range of $^{89}$Zr product volume fractions ranging from 1.3 to 3.7%; H$_2$C$_2$O$_4$ and Na$_2$CO$_3$ additions varied, but their concentrations were equimolar so that complete solution neutralization was achieved, and solutions were diluted with H$_2$O. Whereas a single $^{89}$Zr/Dfo-m transchelation curve was generated for Foil 3, duplicate and triplicate curves of different transchelation solution mixtures were generated for Foils 4 and 5, respectively. The mean [M$_B$] value was determined to be 115±27 nmole·g$^{-1}$, with an ESA of 1180±190 Ci·mmole$^{-1}$.

In contrast, Method 2 employed a consistent 10% volume fraction between $^{89}$Zr product and the buffered Dfo-m transchelation mixture. The only H$_2$C$_2$O$_4$ added to the experiment was from the $^{89}$Zr product, which resulted in a final H$_2$C$_2$O$_4$ concentration of 80 mM. Across the three foils evaluated, Method 2 provided consistent [M$_B$] values averaging 43±7 nmole·g$^{-1}$. ESA was calculated as 2940±600 Ci·mmole$^{-1}$. The [M$_B$] and ESA results for Methods 1 and 2 were within a factor of ~2.5 of each other, thus providing good agreement.

While the ESA term is used ubiquitously in reporting medical isotope quality, it cannot be used to compare isotope products of different activity and/or originating target mass; it is simply the ratio of isotope activity to bindable metals content (M$_B$). The term [M$_B$] expresses the concentration of metals present in the isotope product fraction that compete for binding to the labeling chelate (M$_B$), normalized to the mass of target material from which the isotope is produced. Isotope activity is not considered, because the radioactive isotope produced within the target ($^{89}$Zr=25 nmol/Ci) constitutes an insignificant portion of the competing metal presence (e.g., elemental Zr, Fe, etc.) within the purified product. Consideration of target mass is important, as the target metal (in this case, Y foil) is likely the greatest source of metal impurities introduced into the separation process. Since any given chemical purification process is capable of a finite decontamination of non-Zr metal impurities from the target metal, the use of a lower-mass target should yield a lower M$_B$. Additionally, a lower-mass target will contain less elemental Zr contamination in the $^{89}$Zr product, which should likewise assure a lower M$_B$. Normalizing M$_B$ to the mass of target from which the isotope was produced therefore negates target mass differences and allows for a direct comparison of a purification method's efficacy. This assumes, of course, that the metal contaminant concentrations in high purity Y targets are approximately consistent.

Performance of the tandem column separation method was demonstrated by processing seven cyclotron irradiated Y foil targets. The $^{89}$Zr elution from the secondary column represented 96.8±1.4% of the total activity collected from the dual column process, and 95.1±1.3% of the total activity present in the irradiated foil. The evaluation of replicate $^{89}$Zr elution traces lead to the determination that 90% of the elution activity is found in the first 0.29±0.06 mL of 0.8 M H$_2$C$_2$O$_4$ eluent solution; this elution fraction represents 86±5% of the activity in the irradiated Y foil. This represents an $^{89}$Zr product that is ≥3.5 times more concentrated than that reported by this team and others when performing the traditional single hydroxamate column method. The combination of an increased $^{89}$Zr product concentration (reduced product volume) and reduced H$_2$C$_2$O$_4$ concentration should result in improvements in the labeling performance of $^{89}$Zr onto conjugated mAbs.

In accordance with the materials and methods described herein, $^{89}$Zr compositions are provided that can have bindable metal concentration ([M$_B$]) and effective specific activity (ESA), respectively of less than 169 nmole·g$^{-1}$ and/or greater than 800 Ci·mmole$^{-1}$.

In accordance with example implementations, these compositions can be used as starting materials for methods for radio labeling monoclonal antibodies, other proteins, aptamers, etc.

Methods are also provided for binding $^{89}$Zr to a macromolecule. The methods can include binding the $^{89}$Zr to a nanoparticle and then subsequently binding the $^{89}$Zr-nanoparticle to a macromolecule such as protein including immunoglobulin(s). Accordingly, isotope compositions are provided that can include a radio isotope and a nanoparticle and/or a macromolecule. In accordance with example implementations, the isotope composition can include a radio isotope being one or more of $^{89}$Zr, $^{86}$Y, and/or $^{90}$Y.

In accordance with example implementations, batch contact studies were performed to evaluate the uptake of both $^{88}$Zr and $^{88}$Y (both in the chloride form) onto magnetic iron oxide nanoparticles. Chemically unmodified, commercially available Fe$_3$O$_4$ ("FeO", ~27 nm) and in-house synthesized manganese-doped $Fe_3O_4$ ("MnFeO"), were used. The distribution coefficient values are shown in FIG. 21 ($^{88}Zr$ tracer) and FIG. 22 ($^{88}Y$ tracer) across a range of dilute HCl conditions and in pH-adjusted physiological saline. The results show that the MnFeO has improved $^{88}Zr$ tracer uptake in HCl when compared to FeO. However, FeO is equally effective at $^{88}Zr$ tracer retention in the higher ionic strength physiological saline matrix. For yttrium (as $^{88}Y$ tracer), the overall uptake is lower for FeO and MnFeO in HCl matrix when compared to uptake measured for $^{88}Zr$ at HCl concentrations above 0.001M. A strong pH dependence is shown for $^{88}Y$ tracer in physiological saline, with $K_d$ values at near-neutral saline being very high.

The nanoparticle uptake of highly purified $^{89}Zr$ was obtained directly from the 0.8 M oxalic acid elution matrix. Each of these methods result in $^{89}Zr$ product fractions in the oxalate form (likely as $Zr(C_2O_4)_4^{-4}$). Initial experiments to determine the $K_d$ of $^{88}Zr$ tracer onto the magnetic nanoparticles from oxalic acid resulted in low $K_d$'s (on the order of ~100 mL/g). This distribution coefficient is insufficient for effective isotope loading. Next, the $K_d$'s of $^{88}Zr$ oxalate on the magnetic nanoparticles were determined after the solution was buffered using physiological saline and HEPES buffer. An increase in $^{88}Zr$ tracer binding was observed, with $K_d$ values up to 4700 and 46,000 mL/g for FeO and MnFeO, respectively. This represented a substantial improvement in uptake. However, the $K_d$ values were still substantially lower than those observed in the $ZrCl_4$ system. Therefore, the team evaluated a method to convert the $^{89}Zr$ oxalate product to the chloride form.

In order to obtain the very high $K_d$ values for Zr on the magnetic nanoparticles, as shown in FIG. 21, a method to convert Zr oxalate isotope product to Zr chloride can be utilized. Zirconium oxalate is known to bind strongly to anion exchange (AnIX) resins due to its −4 charge. One approach was to load $Zr(C_2O_4)_4^{-4}$ onto a column, wash excess oxalate from the column, and then elute with HCl to obtain $ZrCl_4$. Both AG MP-1M and QAE-550C resins demonstrated high uptake of $Zr(C_2O_4)_4^{-4}$. Unfortunately, HCl concentrations of >1 M were required to elute the Zr. The magnetic nanoparticles are incompatible with high acid concentrations, as they will dissolve. One option was to evaporate the acid from the $ZrCl_4$ eluent solution and then dissolve the $ZrCl_4$ in a more benign solution. However, there was a risk of hydrolyzing part or all the Zr to the zirconyl ($ZrO^{-2}$) ion during this process.

A modified method was devised to elute Zr from the AnIX column using HCl concentrations as low as 0.15 M HCl. This was accomplished by inserting an intermediate step in the AnIX separation process. $Zr(C_2O_4)_4^{-4}$ was loaded onto a micro-column (27 μL column) packed with a strongly basic anion exchange resin (QAE-550C) that had been previously converted to the oxalate form). Following the load, the column was washed with clean 0.8 M $H_2C_2O_4$, and then the column was converted to the formate form via the addition of formic acid. Zirconium has a high level of retention on the AnIX column in formate form, so it remains fixed on the column during this step.

The formate anion ($HCO_2^-$) has a low "relative selectivity coefficient" on the AnIX resin. For MP-1M resin, formate has a selectivity coefficient of 4.6. This compares to a value of 22 for the chloride anion. An oxalate value is not specified directly in the literature, but it is estimated to be very high—likely somewhere below citrate (220) and above iodide (175). By converting the column from oxalate form (~200) to formate form (4.6), the Zr can be eluted from the AnIX column easily using moderate concentrations of $Cl^-$ ion. FIG. 23 demonstrates the elution of $^{88}Zr$ tracer using HCl between 0.15 and 0.5 M HCl after performing the formate column conversion on QAE-550C strongly basic AnIX resin. Note that when not using the formate conversion step, Zr would not elute from the column unless HCl concentrations of 1 M HCl or greater were utilized. Additionally, even with high HCl eluent concentrations, the Zr elution volumes were significantly greater than those shown in FIG. 23. The formate conversion step resulted in the ability to effectively elute Zr (chloride form) in low volumes (~0.3 to 0.7 mL) of relatively dilute HCl. The addition of a moderate amount of buffering agent to the Zr chloride eluent would assure that dissolution of the iron oxide-based magnetic nanoparticles (MNPs) would not occur, or that damage to labeling proteins would not occur, for example.

Given the new column method to produce $ZrCl_4$ from $Zr(C_2O_4)_4^{-4}$, efficient labeling of the magnetic nanoparticles was now possible. The above chemical method was used to convert purified $^{88}Zr$ tracer from the oxalate form to the chloride form as a necessary step in order to successfully label the isotope onto the magnetic nanoparticles. $^{88}Zr$ tracer was eluted with HCl concentrations of 0.15 M and 0.3 M. Additionally, the $^{88}Zr$ tracer was eluted with 0.15 M and 0.3 M HCl that was diluted 1:1 with phosphate buffered saline (PBS). Prior to conducting batch contact experiments to determine the distribution coefficients across the various matrices, each of the four $^{88}Zr$ tracer eluent solutions was diluted again into PBS. The final PBS dilution, resulting pH, and chloride concentration is indicated in Table 14.

TABLE 14

Measured distribution coefficients ($K_d$s) for Zr (as $^{88}ZrCl_4$) loaded onto $Fe_3O_4$ (FeO) and Mn-doped $Fe_3O_4$ (MnFeO) magnetic nanoparticles from a range of HCl concentrations diluted into phosphate buffered saline (PBS).

| Trial ID | Zr Eluent | Zr Eluent Dilution into PBS, v/v | pH | [Cl⁻], M | Log $K_d$, mL/g (% Loading) FeO | MnFeO |
|---|---|---|---|---|---|---|
| 1 | 0.3 M HCl | 1:2 | 1.03 | 0.194 | 4.2 (88) | 5.2 (99) |
| 2 | 0.15 M HCl | 1:2 | 1.35 | 0.144 | 4.9 (95) | 5.2 (98) |
| 3 | 0.3 M HCl + PBS [a] | 1:2 | 1.37 | 0.194 | 4.2 (90) | 5.2 (99) |
| 4 | 0.15 M HCl + PBS [a] | 1:2 | 1.75 | 0.144 | 5.2 (99) | 5.3 (99) |

TABLE 14-continued

Measured distribution coefficients ($K_d$s) for Zr (as $^{88}ZrCl_4$) loaded onto $Fe_3O_4$ (FeO) and Mn-doped $Fe_3O_4$ (MnFeO) magnetic nanoparticles from a range of HCl concentrations diluted into phosphate buffered saline (PBS).

| Trial ID | Zr Eluent | Zr Eluent Dilution into PBS, v/v | pH | [Cl⁻], M | Log $K_d$, mL/g (% Loading) FeO | Log $K_d$, mL/g (% Loading) MnFeO |
|---|---|---|---|---|---|---|
| 5 | 0.15 M HCl + PBS [a] | 1:3 | 1.91 | 0.143 | 5.2 (99) | 5.3 (99) |
| 6 | 0.15 M HCl + PBS [a] | 1:4 | 1.96 | 0.143 | 5.1 (99) | 5.5 (99) |

[a] HCl solution diluted 1:1 into PBS prior to column elution.

Measured distribution coefficient values are presented as Log $K_d$; percent $^{88}$Zr tracer uptake values are listed in parentheses.

Within the solutions, which ranged between pH 1 and pH 2, the FeO and MnFeO nanoparticles were observed to be relatively stable over the contact period. For MnFeO MNPs, a 1 h contact time resulted in <1% Fe mass solubilization and ~17% Mn mass solubilization fractions. Despite the loss of Mn from the MnFeO MNP media, however, the material was still capable of analyte sorption.

Distribution coefficient values for both nanoparticle types were very high, with $K_d$'s typically measured at levels exceeding 10,000 mL/g for FeO and exceeding 100,000 mL/g for MnFeO. The $K_d$ values are in good agreement with those observed in a matrix of pH-controlled physiological saline (FIG. 21, Right). This study indicates that the Zr oxalate-to-chloride conversion method is effective at removing oxalate from the Zr eluent, which results in dramatic increases in Zr retention on the MNPs.

The superparamagnetic metal oxides $Fe_3O_4$ and Mn-doped $Fe_3O_4$ were shown to exhibit high affinities for Zr from dilute HCl solutions and solutions of physiological saline across a pH range. Measured affinities in oxalic acid were low, but were improved with the addition of buffering agents.

In accordance with example implementations, wherein $^{89}$Zr is eluted in an oxalate form, for example from a hydroxamate resin alone or from a hydroxamate resin as part of the dual column system described herein, it may be converted to a chloride form. A column method was developed in order to convert the $^{89}$Zr oxalate product fraction to $^{89}ZrCl_4$, using formic acid to enable efficient $^{89}$Zr elution from the column using a low concentration of HCl. This resulting eluent solution, diluted into PBS, demonstrated that $^{89}$Zr $K_d$ values were high for FeO (10,000 to >100,000 mL/g) and very high for MnFeO (>100,000 mL/g).

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A method for purifying $^{89}$Zr, the method comprising:
loading a hydroxamate resin column with a loading solution comprising HCl and $^{89}$Zr;
eluting the $^{89}$Zr from the column with an oxalic acid solution having molarity of less than 1 to form a first mixture comprising $^{89}$Zr in oxalate form;
loading another resin with the mixture of $^{89}$Zr in oxalate form;
converting the other resin to formate form; and
eluting the $^{89}$Zr from the other resin to form a second mixture comprising $^{89}$Zr in chloride form.

2. The method of claim 1 further comprising preparing the loading solution from irradiated yttrium.

3. The method of claim 2 wherein the irradiated yttrium was bombarded with accelerated protons.

4. The method of claim 1 wherein the oxalic acid solution is between 0.3 and less than 1 M.

* * * * *

UNITED STATES PATENT AND TRADEMARK OFFICE
CERTIFICATE OF CORRECTION

PATENT NO. : 11,197,938 B1
APPLICATION NO. : 15/788724
DATED : December 14, 2021
INVENTOR(S) : Matthew J. O'Hara It is certified that error appears in the above-identified patent and that said Letters Patent is hereby corrected as shown below:

On the Title Page

(56) References Cited, 2nd Column, 50th Line – Replace
"Specific-Activity Zirconmium-89", Nuclear Medicine and Biology" with
--Specific-Activity Zirconium-89", Nuclear Medicine and Biology--

(56) References Cited, 2nd Column, 57th Line – Replace
"Hudson et al., "Bare Magnetic Nanoparticies: Sustainable Synthesis" with
--Hudson et al., "Bare Magnetic Nanoparticles: Sustainable Synthesis--

(56) References Cited, page 2, 2nd Column, 52nd Line – Replace
"munodiagnostics of Prostrate Cancer", Master of Science Thesis," with
--munodiagnostics of Prostrate Cancer", Master of Science Thesis,--

In the Specification

Column 2, Line 28 – Replace "having a have" with --having a--

Column 7, Line 19 (Table 1) – Replace ""$^a$Foil" with --a. Foil--

Column 7, Line 20 (Table 1) – Replace ""$^b$At" with --b. At--

Column 7, Line 22 (Table 1) – Replace ""$^c$Only" with --c. Only--

Column 8, Line 41 (Table 2) – Replace ""$^a$ At" with --a. At--

Column 8, Line 42 (Table 2) – Replace ""$^b$ Total" with --b. Total--

Column 8, Line 43 (Table 2) – Replace ""$^c$ Foil" with --c. Foil--

Signed and Sealed this
Fourteenth Day of February, 2023

*Katherine Kelly Vidal*
Katherine Kelly Vidal
*Director of the United States Patent and Trademark Office*

CERTIFICATE OF CORRECTION (continued)

Column 8, Line 44 (Table 2) – Replace "$^d$ $^{89}$Zr" with --d. $^{89}$Zr--

Column 8, Line 45 (Table 2) – Replace "$^e$ Sample" with --e. Sample--

Column 10, Line 49 (Table 3) – Replace "$^a$Flow" with --a. Flow--

Column 10, Line 50 (Table 3) – Replace "$^b$V2" with --b. V2--

Column 10, Line 51 (Table 3) – Replace "$^c$Delivered" with --c. Delivered--

Column 11, Line 14 (Table 4) – Replace "$^a$V2" with --a. V2--

Column 11, Line 15 (Table 4) – Replace "$^b$Delivery" with --b. Delivery--

Column 11, Line 16 (Table 4) – Replace "$^c$2 × 0.5" with --c. 2 × 0.5--

Column 11, Line 18 (Table 4) – Replace "$^d$Eluents" with --d. Eluents--

Column 11, Line 19 (Table 4) – Replace "$^e$The" with --e. The--

Column 12, Line 36 (Table 5) – Replace "$^a$$^{88}$Zr" with --a. $^{88}$Zr--

Column 12, Line 37 (Table 5) – Replace "$^b$$^{88}$Zr" with --b. $^{88}$Zr--

Column 12, Line 38 (Table 5) – Replace "$^c$Despite" with --c. Despite--

Column 14, Line 22 (Table 6) – Replace "$^a$Performed" with --a. Performed--

Column 14, Line 23 (Table 6) – Replace "$^b$$^{88}$Zr" with --b. $^{88}$Zr--

Column 15, Line 54 (Table 7) – Replace "$^a$ Activity" with --a. Activity--

Column 15, Line 55 (Table 7) – Replace "$^b$ 0.1 M" with --b. 0.1 M--

Column 15, Line 56 (Table 7) – Replace "$^c$ Activity" with --c. Activity--

Column 15, Line 57 (Table 7) – Replace "$^d$ Combined" with --d. Combined--

Column 15, Line 59 (Table 7) – Replace "$^e$ Fraction" with --e. Fraction--

Column 18, Line 16 – Replace "were remotely by computer" with --were remotely operated by computer--

Column 18, Line 41 – Replace "were assembled into separate." with --were assembled into separate boxes.--

CERTIFICATE OF CORRECTION (continued)
U.S. Pat. No. 11,197,938 B1

Page 3 of 4

Column 19, Line 10 (Table 8) – Replace ""$^a$Flow" with --a. Flow--

Column 19, Line 11 (Table 8) – Replace ""$^b$Sample" with --b. Sample--

Column 19, Line 12 (Table 8) – Replace ""$^c$[NaF]" with --c. [NaF]--

Column 19, Line 48 (Table 9) – Replace "aFor" with --a. For--

Column 19, Line 49 (Table 9) – Replace ""$^b$ Target" with --b. Target--

Column 19, Line 50 (Table 9) – Replace ""$^c$ At" with --c. At--

Column 19, Line 51 (Table 9) – Replace ""$^d$Only" with --d. Only--

Column 22, Line 51 (Table 11) – Replace ""$^a$ Total" with --a. Total--

Column 22, Line 52 (Table 11) – Replace
""$^b$ Cumulative activity fraction across 2 M HCl and H2O washes" with
--b. Cumulative activity fraction across 2 M HCl and H$_2$O washes--

Column 22, Line 53 (Table 11) – Replace ""$^c$ $^{89}$Zr" with --c. $^{89}$Zr--

Column 22, Line 54 (Table 11) – Replace ""$^d$ Strip" with --d. Strip--

Column 24, Line 31 (Table 12) – Replace ""$^a$$^{89}$Zr" with --a. $^{89}$Zr--

Column 24, Line 32 (Table 12) – Replace ""$^b$$^{89}$Zr" with --b. $^{89}$Zr--

Column 24, Line 33 (Table 12) – Replace ""$^c$Buffer" with --c. Buffer--

Column 24, Line 34 (Table 12) – Replace ""$^d$Buffer" with --d. Buffer--

Column 24, Line 36 (Table 12) – Replace ""$^e$Buffer" with --e. Buffer--

Column 25, Line 14 (Table 13) – Replace "83 b" with --83$^b$--

Column 25, Line 19 (Table 13) – Replace ""$^a$ Based" with --a. Based--

Column 25, Line 20 (Table 13) – Replace ""$^b$ Na$_2$CO$_3$" with --b. Na$_2$CO$_3$--

Column 25, Line 21 (Table 13) – Replace ""$^c$ Na$_2$CO$_3$" with --c. Na$_2$CO$_3$--

Column 25, Line 22 (Table 13) – Replace ""$^d$ 89Zr/DFOM" with --d. $^{89}$Zr/DFOM--

Column 25, Line 23 (Table 13) – Replace ""$^e$ Where" with --e. Where--

CERTIFICATE OF CORRECTION (continued)
U.S. Pat. No. 11,197,938 B1

Column 28, Line 58 (Table 14) – Replace "MnFe0" with --MnFeO--

Column 29, Line 8 (Table 14) – Replace "MnFe0" with --MnFeO--

Column 29, Line 14 (Table 14) – Replace "$^a$ HCl" with --a. HCl--